(12) United States Patent
Becker et al.

(10) Patent No.: US 9,587,070 B2
(45) Date of Patent: Mar. 7, 2017

(54) POLYMERIC STRUCTURES CONTAINING STRAINED CYCLOALKYNE FUNCTIONALITY FOR POST-FABRICATION AZIDEALKYNE CYCLOADDITION FUNCTIONALIZATION

(71) Applicants: Matthew Becker, Stow, OH (US); Jukuan Zheng, Akron, OH (US)

(72) Inventors: Matthew Becker, Stow, OH (US); Jukuan Zheng, Akron, OH (US)

(*) Notice: Subject to any disclaimer, the term of this patent is extended or adjusted under 35 U.S.C. 154(b) by 16 days.

(21) Appl. No.: 14/418,649

(22) PCT Filed: Jul. 31, 2013

(86) PCT No.: PCT/US2013/052971
§ 371 (c)(1),
(2) Date: Jan. 30, 2015

(87) PCT Pub. No.: WO2014/022535
PCT Pub. Date: Feb. 6, 2014

(65) Prior Publication Data
US 2015/0197600 A1    Jul. 16, 2015

Related U.S. Application Data

(60) Provisional application No. 61/677,691, filed on Jul. 31, 2012.

(51) Int. Cl.
| | |
|---|---|
| *C08G 63/02* | (2006.01) |
| *C08G 63/91* | (2006.01) |
| *C08G 85/00* | (2006.01) |
| *A61L 27/14* | (2006.01) |
| *A61L 27/38* | (2006.01) |
| *C07C 271/34* | (2006.01) |
| *C08G 69/48* | (2006.01) |
| *C08G 63/685* | (2006.01) |
| *C08G 69/10* | (2006.01) |
| *C08G 63/00* | (2006.01) |
| *D06M 11/58* | (2006.01) |
| *D01F 6/60* | (2006.01) |
| *D01F 6/62* | (2006.01) |

(52) U.S. Cl.
CPC .............. *C08G 63/91* (2013.01); *A61L 27/14* (2013.01); *A61L 27/38* (2013.01); *C07C 271/34* (2013.01); *C08G 63/6852* (2013.01); *C08G 63/912* (2013.01); *C08G 69/10* (2013.01); *C08G 69/48* (2013.01); *C08G 85/004* (2013.01); *A61L 2400/12* (2013.01); *D01F 6/60* (2013.01); *D01F 6/625* (2013.01); *D06M 11/58* (2013.01)

(58) Field of Classification Search
CPC .......... C08L 71/00; C08G 63/91; A61L 27/14
USPC ............. 548/260, 304.1; 568/326, 609, 808; 525/410
See application file for complete search history.

(56) References Cited

U.S. PATENT DOCUMENTS

| | | | |
|---|---|---|---|
| 2007/0258889 A1 | 11/2007 | Douglas et al. | |
| 2010/0210854 A1* | 8/2010 | Popik ..................... | C07C 41/18 548/260 |
| 2012/0172575 A1 | 7/2012 | Boons et al. | |

OTHER PUBLICATIONS

Jun Guo et al. Surface Modification of Polymeric Micelles by Strain-Promoted Alkyne-Azide Cycloadditions; NIH, Chemistry. Dec. 3, 2010; 16(45) pp. 1-14.*
Georgina Such et al. Synthesis and functionalization of Nano engineered Materials using Click Chemistry, Progress in Polymer Science 37, 7 (2012) pp. 1-19.*
Mbua et al. Strain-Promoted Alkyne-azide Cycloadditions (SPAAC), ChemBioChem, 12(12), 2011, pp. 1911-1920.*
Georgina K. Such, et al; Synthesis and functionalization of nanoengineered materials using click chemistry Progress in Polymer Science 37.7 (2012) 1-19.
Guo, Jun, et al.; "Surface Modication of Polymeric Micelles by Strain, Promoted Alkyne Azide Cycloadditions" Chemistry-A—European Journal 16.45 (2010); 1-4.
Mbua. et al; gStrain-Promoted alkyne-azide cycloadditions (SPAAC) reveal new features of glycoconjugate biosysnnthesis?h CHEMBIOCHEM, 12(12) (2011), 1911-1920.

* cited by examiner

*Primary Examiner* — Terressa Boykin
(74) *Attorney, Agent, or Firm* — Renner Kenner Greive Bobak Taylor & Weber

(57) ABSTRACT

A method of creating biocompatible polymeric structures includes the steps of: providing a biocompatible polymer including a strained cycloalkyne end group; forming a polymeric structure from the biocompatible polymer such that the strained cycloalkyne end group remains on the biocompatible polymer; providing an azide tethered molecule; and, after forming the polymeric structure, reacting the azide tethered molecule with the cycloalkyne in an azide alkyne cycloaddition reaction to further functionalize the polymeric structure.

17 Claims, 13 Drawing Sheets

POLYMERIC STRUCTURES CONTAINING STRAINED CYCLOALKYNE FUNCTIONALITY FOR POST-FABRICATION AZIDEALKYNE CYCLOADDITION FUNCTIONALIZATION

CROSS-REFERENCE TO RELATED APPLICATION

This application claims priority to U.S. Patent Provisional Application No. 61/677,691 filed on Jul. 31, 2012, the contents of which are incorporated herein by reference.

FIELD OF THE INVENTION

The present invention generally resides in the art of biocompatible polymeric structures. More particularly, the present invention relates to biocompatible polymeric structures bearing strained cycloalkyne functionality that survives the process of fabricating the polymeric structures. The cycloalkyne functionality can be beneficially employed in a post-fabrication functionalization through azide-alkynecyclo addition.

BACKGROUND OF THE INVENTION

For more than two decades, tremendous advances in regenerative medicine have provided hope that materials will offer solutions to organ and tissue shortages that occur worldwide. However, overcoming the remaining challenges will require many additional innovations, especially in materials that possess specific functionality that guide the regenerative processes.

Nanofibrous scaffolds possessing mechanical properties, porous microstructure, and dimensional similarity to collagen fibers have been used to mimic the natural extracellular matrix (ECM) and are highly relevant for tissue engineering in a number of different applications. Polymeric nanofibers have been fabricated into a variety of constructs and scaffolds using melt- or electrospinning processes that are able to control size, morphology and alignment by varying conditions including solvent, concentration, additives and electrode design.

For regenerative medicine applications, the polymeric precursors used to fabricate the nanofiber-based scaffolds should be both biocompatible and biodegradable. Many biodegradable and biocompatible polymers such as polyglycolic acid (PGA), poly(lactic acid) (PLA), poly(lactide-co-glycotide) (PLGA) and poly($\epsilon$-caprolactone) (PCL) have been widely investigated as fiber and nanofiber precursor materials. Although these degradable polymers meet several of the basic requirements for tissue engineering applications, bioactive molecules to guide cellular behavior and preserve cell phenotype are required for optimal performance. Specific functionalities that could guide or direct specific biological function need to be incorporated efficiently. There are generally two methods available for biomolecule functionalization: physical adsorption and chemical bonding. While physical adsorption risks the loss of biomolecules over time, chemical conjugation usually requires multi-step processing, and purification both of which often included harsh conditions.

Additionally, the derivitization of nanofibers often requires multiple procedures, including plasma treatment, wet chemical methods, surface graft polymerization, and co-electrospinning of surface active agents with polymers. Each of these modifications is time and resource intensive to optimize and may lead to immune specific reactions and biocompatibility problems.

A new method that enables efficient, orthogonal and bio-system friendly functionalization is preferred. Copper-catalysed click chemistry has been used for efficient functionalization of polymers. However, the side effect of copper ions leads to biocompatibility problems. Recently, the discovery of strain-promoted azide alkyne cycloaddition has provided a robust chemical method for the efficient conjugation of biomolecules. This method has been widely used in bioimaging and bioconjugation. The present invention makes beneficial use of this click chemistry and provides guidance for the creation of fibrous scaffolds and their post fabrication biofunctionalization through such azide alkyne cycloaddition chemistry.

Peptides, growth factors and carbohydrates have each been covalently tethered to the surfaces of synthetic and naturally-derived polymers to stimulate specific cell functions. Concerns about the bioavailability, specificity and activity of the tethered species persist. Recent studies show that the desired biological response can be obtained with the appropriate tether. A number of synthetic degradable polymers, including poly(lactic acid) are presently utilized clinically; but, cellular systems do not readily interact directly with synthetic polymers through normal integrin mediated assemblies. Tyr-Ile-Gly-Ser-Arg (YIGSR), a bio-active peptide derived from laminin, was shown to promote cell attachment and laminin receptor binding. Graf, J.; Ogle, R. C.; Robey, F. A.; Sasaki, M.; Martin, G. R.; Yamada, Y.; Kleinman, H. K. Biochemistry 1987, 26, 6896-6900. YIGSR-functionalized matrices have showed similar or superior cellular effects to Ile-Lys-Val-Ala-Val (IKVAV) peptide, a more commonly studied laminin-derived peptide and laminin-coated matrices. The art could benefit from incorporating YIGSR into nanofibers matrices to promote the directed differentiation of embryonic stem cells into neurons. However, the precise, regiospecific functionalization of degradable polymers with biological motifs capable of directing cellular function has been so complicated with regard to solvents, catalysts, residuals and processing methods, that they have been deemed translationally irrelevant. The recent evolution of click chemistry as a method to functionalize polymers and materials has enabled the derivatization of both natural and synthetic polymers in ways that were not previously possible.

SUMMARY OF THE INVENTION

A first embodiment of this invention provides a method of creating biocompatible polymeric structures comprising the steps of: providing a biocompatible polymer including a strained cycloalkyne end group; forming a polymeric structure from the biocompatible polymer such that the strained cycloalkyne end group remains on the biocompatible polymer; providing an azide tethered molecule; and, after said step of forming, reacting the azide tethered molecule with the cycloalkyne in an azide alkyne cycloaddition reaction to further functionalize the polymeric structure.

A second embodiment provides a method as in the first embodiment, wherein said step of providing a biocompatible polymer includes the step of polymerizing monomers through a ring-opening polymerization employing a ROP initiator having a strained cycloalkyne to create the biocompatible polymer including a strained cycloalkyne end group.

A third embodiment provides a method as in the first or second embodiment, wherein the ROP initiator includes a five to nine member strained cycloalkyne.

A fourth embodiment provides a method as in any of the first through third embodiments, wherein the ROP initiator further includes a reactive group selected from an hydroxyl group or amine group.

A fifth embodiment provides a method as in any of the first through fourth embodiments, wherein the reactive group is an hydroxyl group, and the monomers polymerized in said step of polymerizing are cyclic esters.

A sixth embodiment provides a method as in any of the first through fifth embodiments, wherein the reactive group is an hydroxyl group, and the monomers polymerized in said step of polymerizing are selected from lactones, lactides and glycolides.

A seventh embodiment provides a method as in any of the first through sixth embodiments, wherein the reactive group is an amine, and the monomers polymerized in said step of polymerization are N-carboxylic anhydrides.

An eighth embodiment provides a method as in any of the first through seventh embodiments, wherein the ROP initiator includes an 8-member cycloalkyne.

A ninth embodiment provides a method as in any of the first through eighth embodiments, wherein the ROP initiator is selected according to the following structure:

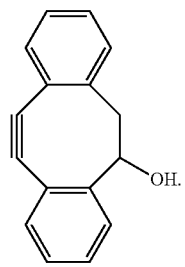 [SMILES: OC1Cc2ccccc2C#Cc2ccccc21]

A tenth embodiment provides a method as in any of the first through ninth embodiments, wherein the ROP initiator is selected according to the following structure:

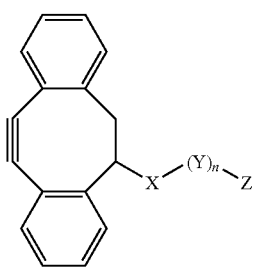

wherein X is a urethane or carbonate, Y is methylene (CH2) group or ethoxy ($CH_2CH_2O$) group, n is from 1 or more to 12 or less, and Z is an amine or hydroxyl or hydroxyethyl.

An eleventh embodiment provides a method as in any of the first through tenth embodiments, wherein the ROP initiator is selected according to the following structure:

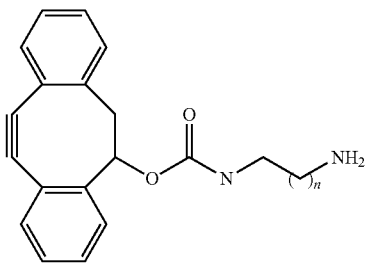

wherein n is from 1 to 5.

A twelfth embodiment provides a method as in any of the first through eleventh embodiments, wherein the ROP initiator is selected according to the following structure:

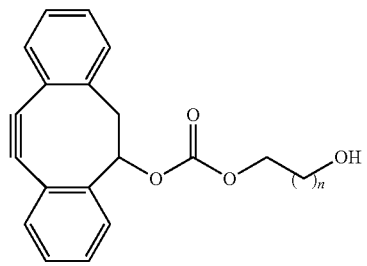

wherein n is from 1 to 11.

A thirteenth embodiment provides a method as in any of the first through twelfth embodiments, wherein the ROP initiator is selected according to the following structure:

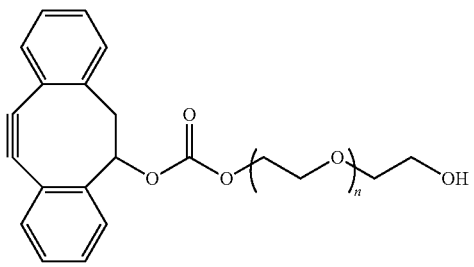

wherein n is from 1 to 5.

A fourteenth embodiment provides a method as in any of the first thirteenth embodiments, wherein said step of forming a polymeric structure includes processes selected from the group consisting of electrospinning, melt-blowing, salt leach scaffolding, nanofibers by gas jet, ink jet printing and 3d printing.

A fifteenth embodiment provides a method as in any of the first through fourteenth embodiments, wherein the strained cycloalkyne survives said step of forming.

A sixteenth embodiment provides a method as in any of the first through fifteenth embodiments, further including the step of storing the polymeric structure after said step of forming so as to preserve the strained cycloalkyne end group, and performing said step of reacting an azide tethered molecule after said step of storing such that the further functionalization of said step of reacting is carried out as functionalization is needed and such functionalization can be tailored to a desired functionality.

A seventeenth embodiment provides a method as in any of the first through sixteenth embodiments, wherein the azide-functionalized group is selected from the group consisting of azide-functionalized DNA, azide-functionalized peptides, azide-functionalized proteins, azide-functionalized sugars, azide-functionalized metal, azide-functionalized nanoparticles and azide-functionalized antimicrobials.

An eighteenth embodiment provides a ring opening polymerization initiator according to the following structure:

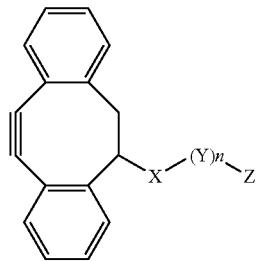

wherein X is a urethane or carbonate, Y is methylene ($CH_2$) group or ethoxy ($CH_2CH_2O$) group, n is from 1 or more to 12 or less, and Z is an amine or hydroxyl or hydroxyethyl.

A nineteenth embodiment provides a ring opening polymerization initiator according to the following structure:

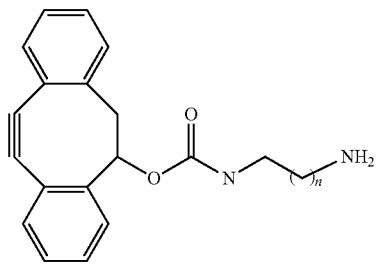

wherein n is 5.

DETAILED DESCRIPTION OF ILLUSTRATIVE EMBODIMENTS

Figure 1:
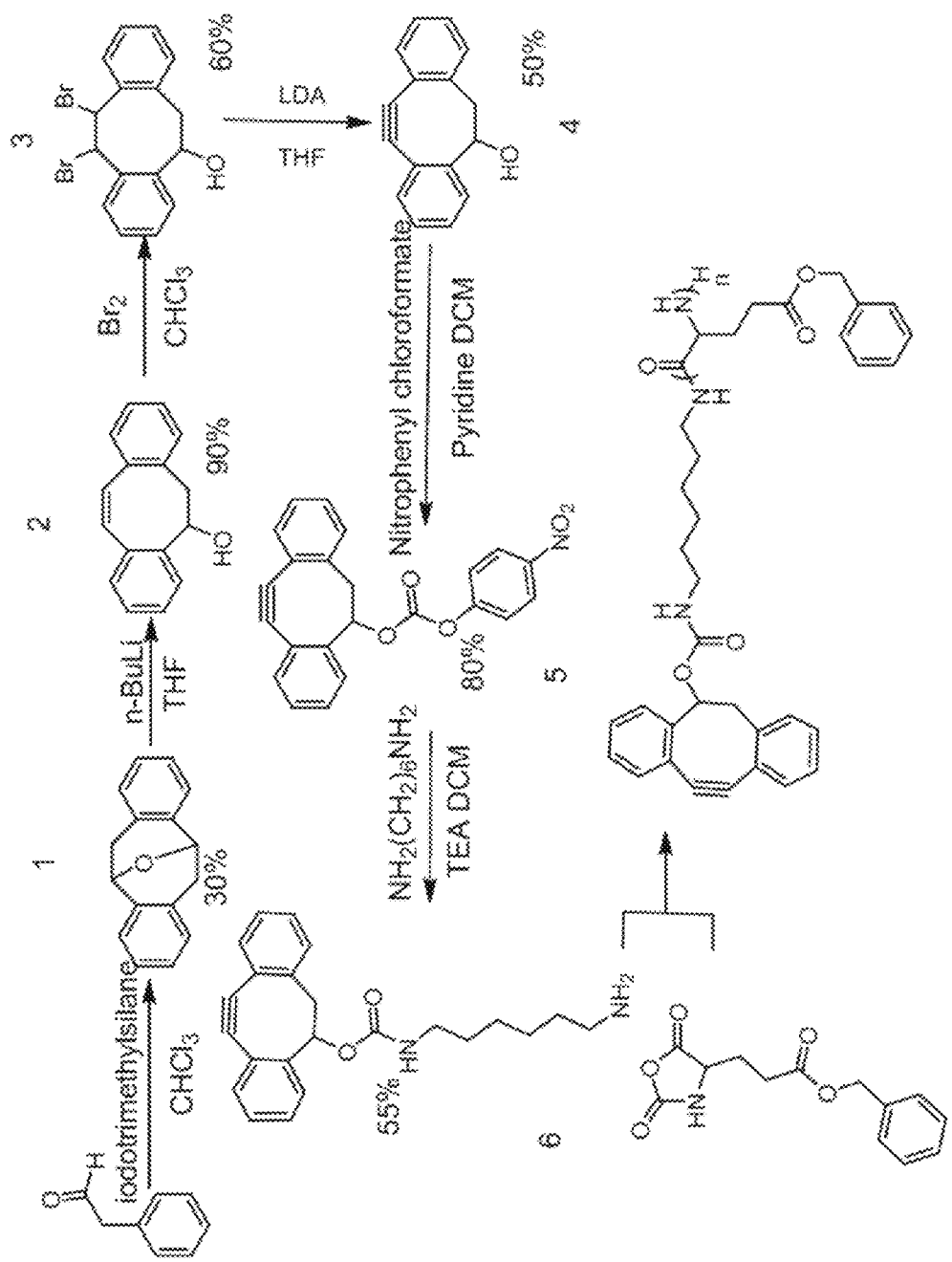
FIG. 1 is the reaction scheme for the synthesis of dibenzocyclooctynol-functionalized Poly(γ-benzyl-L-glutamate) (DIBO-PBLG).

The present invention provides methodologies for creating polymeric structures formed of polymers having strained cycloalkyne functionality that survives the creation process. After creation of the polymeric structure, the polymers are functionalized through strain-promoted azide alkyne cycloaddition copper free "click" chemistry. The polymeric structures bearing cycloalkyne functionality can be stored and post-functionalized as needed though simple well defined azide alkyne cycloaddition copper free "click" chemistry.

The polymeric structures are formed at least in part of a biocompatible polymer including a strained cycloalkyne end group. As used herein, a strained cycloalkyne is a five to nine member or greater cycloalkyne. In some embodiments, the strained cycloalkyne includes an 8-member cycloalkyne. In some embodiments, the 8-member cycloalkyne is a 4-dibenzocyclooctyne end group (DIBO end group).

In some embodiments, the cycloalkyne is an end group on a biocompatible and biodegradable polymer selected from polyglutamates, polylactones, polylacatides, polyglycolides and copolymers of any of the forgoing.

In some embodiments, the cycloalkyne is an end group on a polymer selected from poly-gamma-benzyl-L-glutamate, polycaprolactone, polylactic acid, and polyglycolide and copolymers of any of the forgoing. In some embodiments, cycloalkyne is an end group on a co-polymer selected from poly(lactide-co-glycolide), poly(lactide-co-caprolactone), poly(caprolactone-co-glycolide), and poly(caprolactone-co-3-ketocaprolactone).

In some embodiments, the biodegradable and biocompatible polymers having a cycloalkyne end group are formed by ring-opening polymerization (ROP). These polymerizations employ what are termed herein "ROP initiator(s)" having a strained cycloalkyne as defined above. In some embodiments, the strained cycloalkyne includes an 8-member cycloalkyne. In some embodiments, the 8-member cycloalkyne is a 4-dibenzocyclooctyne (DIBO) group.

Notably, the ROP method of forming the polymer with cycloalkyne end group is particularly beneficial because cycloalkyne is not typically used as an initiator, and, in the case of biocompatible and biodegradable polymers, it provides a method of functionalizing them, which the skilled artisan recognizes as being difficult to do. The strained cycloalkyne enables the artisan to derivatize the degradable polymer using conditions that do not require catalyst or additives and do not degrade the polymer. Using DIBO as an initiating system allows the artisan to control the stoichiometry of functional species in the polymer using molecular mass of the polymer as there is one functional group per chain.

In some embodiments, the ROP initiator includes a strained cycloalkyne and has a reactive group selected from an hydroxyl group and an amine group. With hydroxyl functionality, the ROP initiator is suitable for the ring opening polymerization of cyclic esters, such as lactones, lactides and glycolides. With amine functionality, the ROP initiator is suitable for the ring opening polymerization of monomers bearing N-carboxylic anhydrides, such as γ-benzyl-L-glutamate N-carboxyanhydride.

In some embodiments, the cyclic esters are 5 to 9 member cyclic lactones. In some embodiments, the cyclic lactone is selected from ε-caprolactone, 1,4,8-trioxaspiro[4.6]-9-undecanone, γ-butyrolactone, and δ-calerolactone.

In some embodiments, the monomer is selected from glycolic acid and glycolide.

In some embodiments, the monomer is selected from lactide and lactic acid.

In some embodiments, the ROP initiator is selected from 4-dibenzocyclooctynol (DIBO):

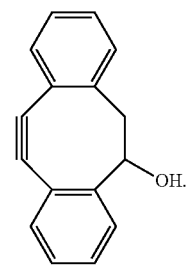 [SMILES: OC1Cc2ccccc2C#Cc2ccccc21]

In some embodiments, the ROP initiator is selected from DIBO derivatives thereof. In some embodiments, the ROP initiator is an amine-functionalized DIBO derivative or hydroxy-functionalized DIBO derivative. In some embodiments, the ROP initiator is chosen according to the following structure:

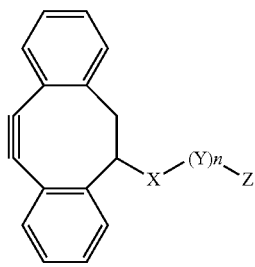

wherein X is a urethane or carbonate linkage, Y is methylene ($CH_2$) group or ethoxy ($CH_2CH_2O$) group, n is from 1 or more to 12 or less, and Z is an amine or hydroxyl or hydroxyethyl.

In some embodiments, X is a urethane linkage, Y is methylene, n is from 1 to 5, and Z is an amine, such that the ROP initiator has the following structure:

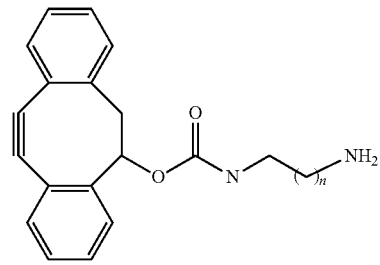

In a particular embodiment thereof, n is 5.

In some embodiments, X is a carbonate linkage, Y is methylene, n is from 1 to 11, and Z is an hydroxyl, such that the ROP initiator has the following structure:

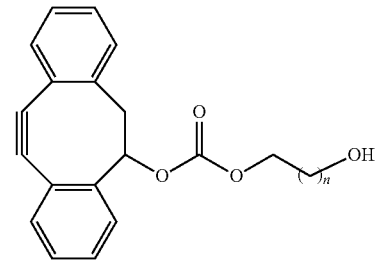

In a particular embodiment thereof, n is from 1 to 6.

In some embodiments, X is a carbonate linkage, Y is $CH_2CH_2O$, n is from 1 to 5, and Z is an hydroxyethyl, such that the ROP initiator has the following structure:

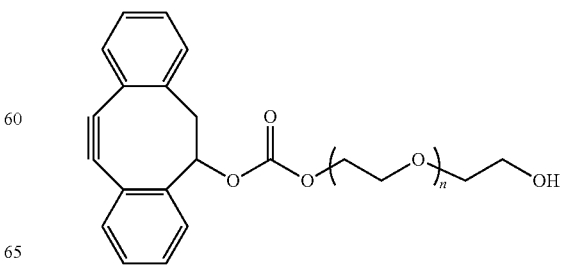

In a particular embodiment thereof, n is 5.

In some embodiments, ε-caprolatone monomers are polymerized through ROP by use of DIBO, above. In some embodiments, γ-benzyl-L-glutamate N-carboxyanhydride is polymerized through ROP by use of:

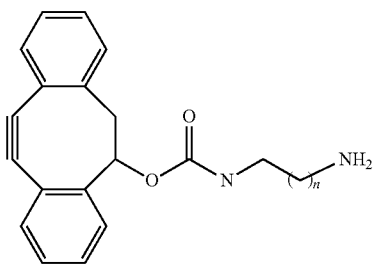

wherein n is 5. In some embodiments, 1-lactide monomers are polymerized though ROP by use of DIBO. In yet other embodiments, DIBO is used as the initiator for the ring-opening copolymerization of ε-caprolactone and 1,4,8-trioxaspiro[4.6]-9-undecanone (TOSUO) to yield the DIBO-(P(CL-co-OPD)).

The polymers bearing cycloalkyne end groups are formed into polymeric structures. These structures may be formed in any suitable manner taking into account the properties and limitations of any given polymer (e.g., solubility and heat stability). In some embodiments, the polymers bearing cycloalkyne end groups are formed into polymeric structures by methods selected from electrospinning, melt-blowing, salt leach scaffolding, nanofibers by gas jet, ink jet printing and 3d printing.

In some embodiments, the polymers bearing cycloalkyne end groups are electrospun to form fibrous structures. Electrospinning is a well know process in which the polymer bearing cycloalkyne functionality is dissolved in an appropriate solvent, the resulting electrospinning solution is charged and drawn from a spinnerette to a grounded collector, and a fibrous mat is formed in the shape of the collector. In some embodiments, the electrospinning process can be used to create a porous fibrous matrix of biodegradable and biocompatible polymers bearing the strained cycloalkyne functionality.

Suitable solvents will be apparent to those of ordinary skill in the art. In some embodiments, the solvent is selected from aqueous solutions containing 10-50% ethanol or aqueous solutions containing 10-50% methanol.

By choosing suitable fabrication processes for forming polymeric structures, the cycloalkyne end group functionality survives the fabrication process. This functionality is then available for post-fabrication functionalization through azide alkyne cycloaddition copper free "click" chemistry. The click chemistry is well known, and, a desired functionality can be imparted to the polymer by employing azide tethered molecules for reaction with the alkyne through cycloaddition. As used herein, and azide tethered molecule is a molecule that bears a reactive azide group.

In particular embodiments, the azide-tethered molecule is selected from the group consisting of azide-functionalized DNA, azide-functionalized peptides, azide-functionalized proteins, azide-functionalized sugars, azide-functionalized metal, azide-functionalized nanoparticles and azide-functionalized antimicrobials.

The polymeric structures of this invention can be stored after they are fabricated and the strained cyclooctyne end group preserved. Thus the polymeric structures can be functionalized as needed. Thus stock polymeric structures can be tailored to desired end uses with specifically chosen azide-tethered molecules. The strained cyclooctyne reacts only with azide groups. Therefore any conditions where the strained cyclooctyne is available and the azide functionalized molecule is soluble will result in a covalent cyclization. It occurs within a few minutes at room temperature and the rate of reaction increases with increasing temperature.

These and other aspects of this invention are experimentally evidenced by aspects of the following experiments.

EXPERIMENTAL

Example 1

Post-Assembly Derivatization of Electrospun Nanofibers Via Strain-Promoted Azide Alkyne Cycloaddition In this work, 4-dibenzocyclooctynol (DIBO) functionalized with a primary amine group was used as an initiator for the ring opening polymerization of γ-benzyl-L-glutamate N-carboxyanhydride (Bz-L-GluNCA) to yield a 4-dibenzocyclooctynol functionalized poly(γ-benzyl-L-glutamate) (DIBO-PBLG). PBLG is a versatile, degradable material that can adopt α-helix and β-sheet conformations, which is being investigated for cell adhesion and proliferation when used with protein pre-adsorption techniques. The high binding affinity of calcium to PBLG is also promising for bone regeneration applications.

The DIBO-PBLG was synthesized as described in FIG. 1. The strained DIBO precursor was synthesized according to previously described methods. The DIBO was derivatized with p-nitrophenyl chloroformate and further reacted with excess hexamethylene diamine to yield the primary amine-derivatized DIBO compound, 6 (FIG. 1). γ-Benzyl-L-glutamate-N-carboxyanhydride (Bz-L-GluNCA) was synthesized and purified by flash chromatography according to previously reported procedures.

Figure 2:
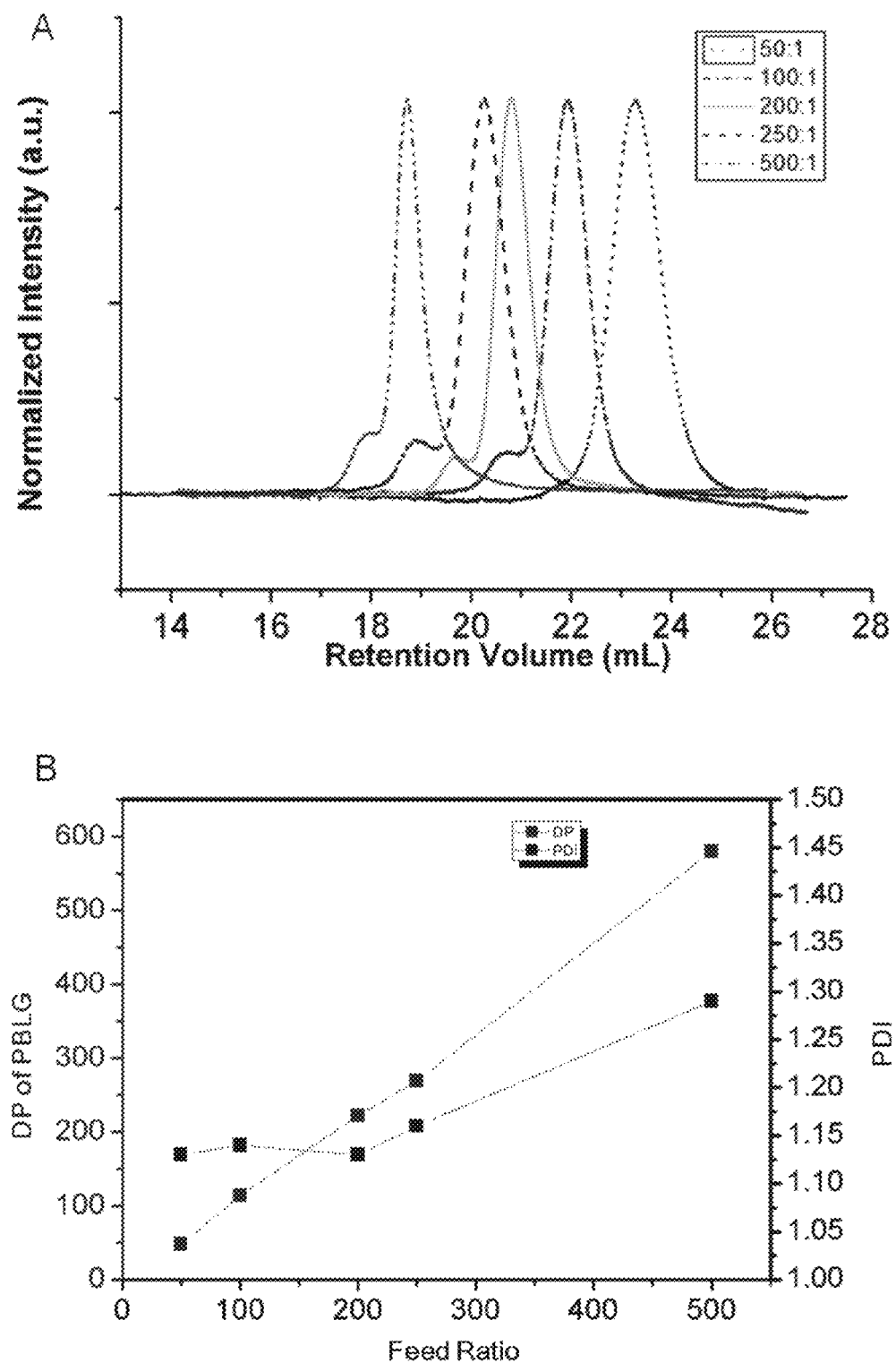
FIG. 2 provides SEC results of DIBO-PBLG with different feed ratios. SEC was run in DMF with LiBr (0.1 mol/L) under 50° C.

The DIBO initiator was used immediately after purification. In a series of polymerizations the amine derivatized DIBO was used as an initiator for the ring opening polymerization of Bz-L-GluNCA in anhydrous DMF under nitrogen for 3 days to yield DIBO functionalized PBLG. The molecular weight of DIBO-PBLG increased linearly with increasing feed ratio from 50:1 to 500:1. The corresponding molecular weight distribution increased from 1.14 to 1.29, which demonstrated that these polymerizations are well controlled and exhibit linear growth kinetics with increasing feed ratio. The various feed ratio conditions and the resulting molecular weights and molecular weight distributions of the resulting polymers were measured via DMF phase SEC and are shown in FIG. 2. The high molecular mass shoulders which appear at increasing feed ratios are consistent with what has been reported by others using amine based initiators for the polymerization of PBLG and is most likely due to water initiated polymer.

The DIBO-derivatized PBLG was then used as a functional precursor for electrospinning of nanofibers to generate a copper-free clickable scaffold. DIBO-PBLG (Mn=128K, PDI=1.29) and the unmodified PBLG (mol wt 150,000-350,000, Sigma) were both prepared in a 12 wt % 1,4-dioxane solution. Each polymer solution was held in a glass pipette and was electrospun from the orifice having an inner diameter of 300 μm at the tip. The electric potential was 6 kV over a 22 cm tip-to-collector distance for the modified polymer, and 12 kV over a 27 cm tip-to-collector distance for the unmodified polymer. A proper positive air pressure was applied on the surface of the solution to maintain the feeding rate. Fibers were collected on conductive glass slides for the subsequent fluorescence measurements, on silicon wafers for SEM observation, and on copper grids for TEM observation. Each type of collector was placed on top of a large grounded aluminum foil mat for the collection of electrospun fibers. Samples were silver coated with a sputter coater (by SPI Supplies, Pennsylvania, U.S.A.) before the SEM observation. From SEM micrographs, it was observed that fibers were obtained with diameters near 1 μm.

Figure 3:
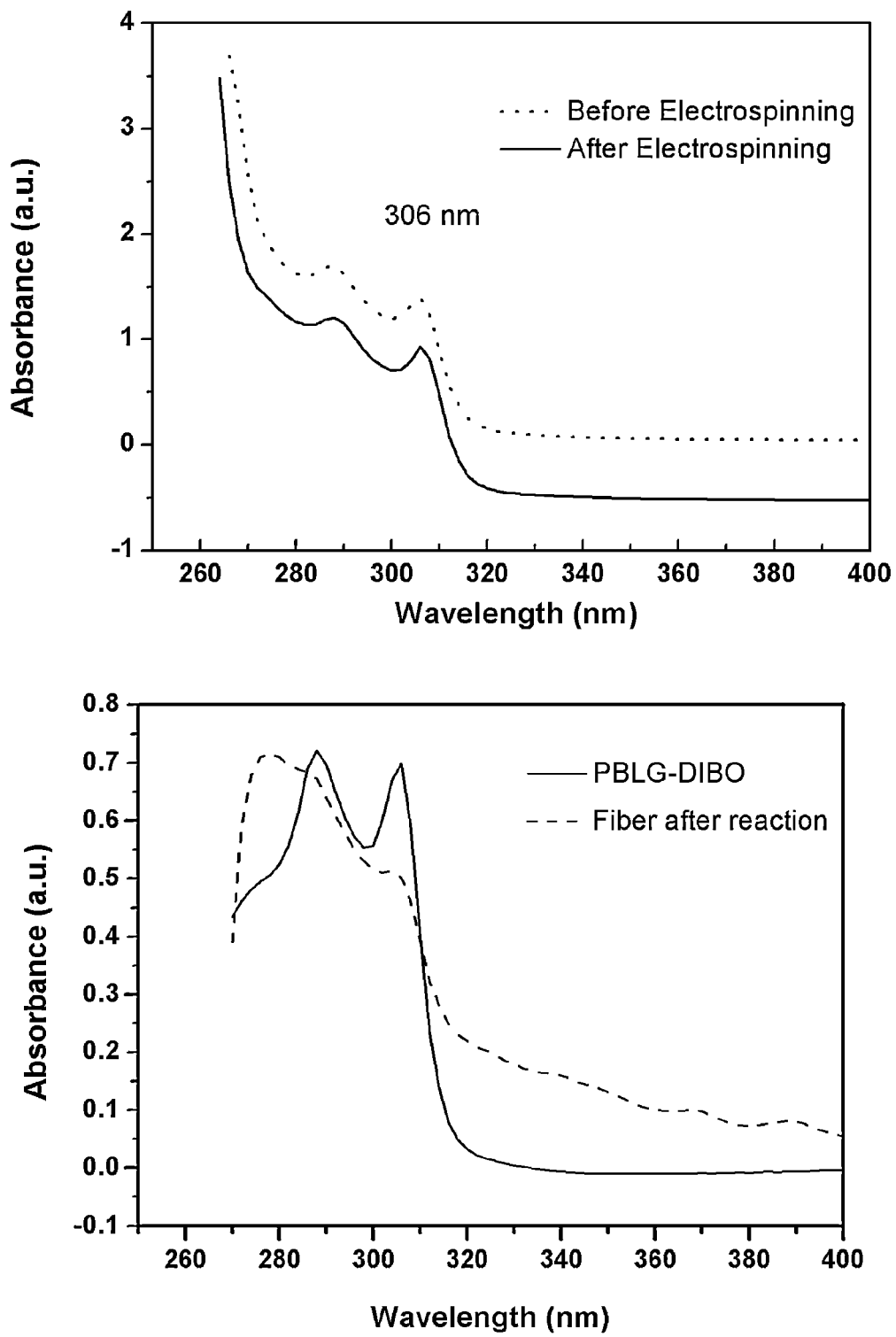
FIG. 3 provides UV spectra of DIBO-PBLG before and after electrospinning indicating that the strained cyclooctyne survives the scaffold fabrication process (top). A second experiment measuring the residual DIBO left following a cycloaddition reaction indicates approximately 26% of the groups were able to react (bottom).

To confirm the survival of the strained DIBO group following the electrospinning process, the fibers were dissolved in DMF and UV-Visible spectra of the solutions showed the presence of optical transitions near 306 nm which correspond to the alkyne group in DIBO (FIG. 3) before and after the fabrication process. Having confirmed the survival of DIBO group through electrospinning, the availability of DIBO on the surface of fibers for biofunctionalization was next investigated.

The extent of DIBO available on the surface of the nanofibers to react was quantified using UV-visible spectroscopy. A solution of 9-methyleneazidoanthracene in methanol, with is a non-solvent for PBLG was allowed to react with a mat of electrospun fibers. Concurrently, a solution of 9-methyleneazidoanthracene in N,N-dimethyl formamide, with is a good solvent for PBLG was allowed to react with an equivalent solution of the DIBO-initiated PBLG. The absorbance of the nanofiber post-functionalization and PBLG-DIBO with identical concentrations were measured following the reaction and from the reduction in absorbance of the alkyne transition in DIBO, the fraction of the DIBO group on the surface of fiber which is available for derivatization is 26±5%.

A post-assembly experiment utilizing an azide containing fluorescence probe (Chremo 488 azide) was conducted. A glass coverslip containing fibers was immersed in a 0.4% (mg/mL) solution of fluorescence probe for 5 min. Following the brief incubation, the fiber-loaded coverslip was removed, washed with methanol and dried under nitrogen. Using fluorescence microscopy, it was found that the azide functionalized fluorescence probe reacted with DIBO group on the surface of fibers. Underivatized PBLG exhibited no fluorescence following the methanol. These experiments indicate the availability of the DIBO groups on the surface for functionalization through strain-promoted azide-alkyne cycloaddition.

Figure 4:
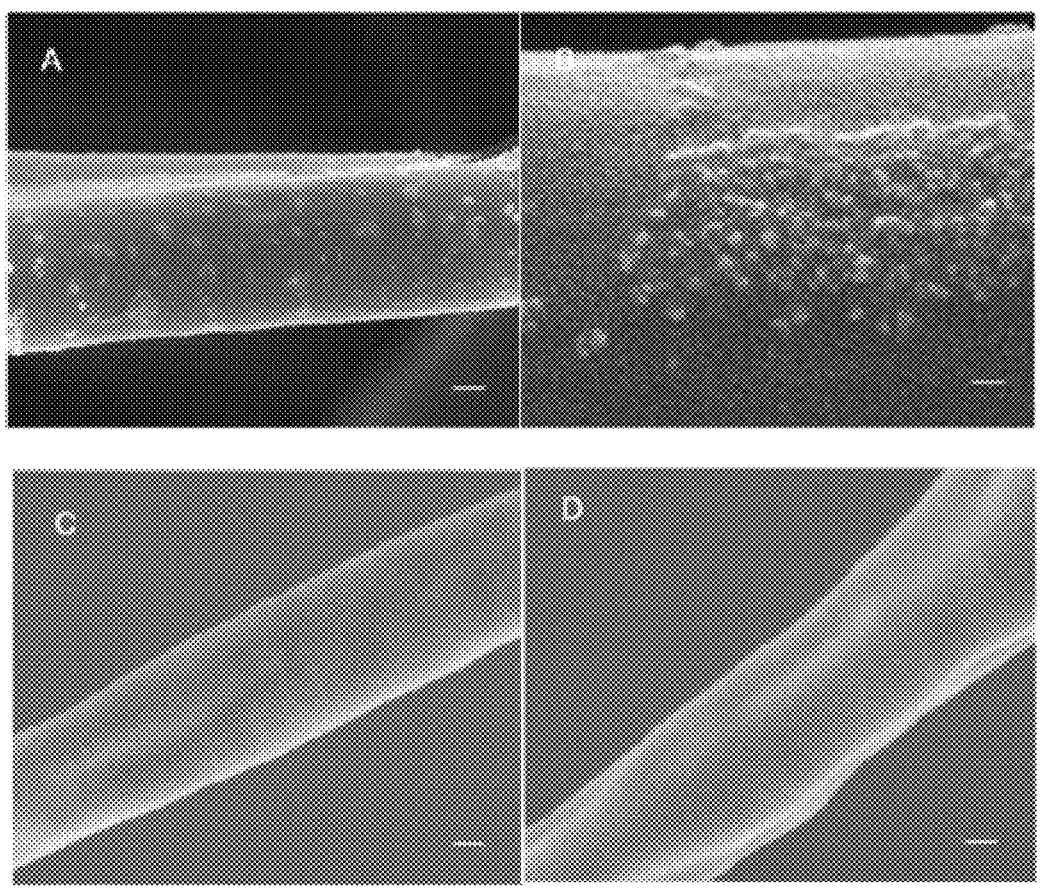
FIG. 4 provides SEM micrographs of gold nanoparticle (50 nm) functionalized fibers (A, B) and unmodified fibers as control (C, D). The scale bar for image A, B, C, D is 600 nm, 100 nm, 300 nm, and 200 nm respectively.

Further proof of the existence of DIBO group on the surface of the fibers was obtained from SEM micrographs of the fibers following immersion in a solution of azide functionalized gold nanoparticles. Fiber loaded silicon wafers were immersed in a solution of azide functionalized gold nanoparticles (50 nm, Nanocs, diluted 500 times) for 5 h, after which the wafer was washed with nanopure water (18 MΩ/cm−1) and dried under vacuum. The SEM images clearly showed the presence of gold nanoparticles on the surface of the fibers, which confirmed that the DIBO group on the surface of fibers are available for functionalization (FIG. 4). A control experiment was performed using fibers composed of unmodified PBLG which showed conclusively that the nonspecific physical adsorption of gold nanoparticles to the surface of fibers is negligible (FIG. 4).

Additional experiments with transmission electron microscopy (TEM) confirmed the existence and availability of DIBO groups on the surface of the fibers. TEM grids loaded with nanofibers were immersed in an azide-functionalized gold nanoparticle solution for 1 h at ambient temperature, after which the grid was washed with nanopure water (18 MΩ/cm$^{-1}$) and dried under vacuum. TEM images showed that gold nanoparticles are present on the surface of the nanofibers. Control experiments with unmodified nanofibers showed that no nonspecific physical adsorption of gold nanoparticles was evident following immersion in the nanoparticle containing solution.

Thus, the utility of an amine-derivatized DIBO unit as an initiator for ring opening polymerization is demonstrated for the first time. Additionally, the DIBO group survives an electrospinning procedure. The resulting nanofiber scaffold is then available for post-assembly functionalization with any number of azide-derivatized molecules. The availability of copper-free click chemistry based biofunctionalization sites on the surface of nanofibers offers versatile approach to create highly functional scaffolds useful in a variety of promising applications in regenerative medicine.

The synthetic details and characterization of the DIBO and amine-derivatized DIBO are included below.

General Methods and Materials

Chemicals and solvents were purchased from Sigma-Aldrich and Acros and were used without further purification. All reactions were performed in anhydrous conditions under an atmosphere of Argon. Flash chromatography was performed on silica gel (Sorbent Technologies Inc., 70-230 mesh). The fluorescence probe Chromeo 488 azide was purchased from Active Motif, the azide functionalized gold nanoparticles (50 nm) was purchased from Nanocs, $^1$H and $^{13}$C NMR spectra were acquired using a Varian NMRS 500 and Varian NMRS 300. UV spectra were measured with Synergy™ MX from BioTek, SEC results were obtained using HLC-8320GPC from TOSOH, SEM images were acquired using JEOL-JSM-7401F with operating voltage as 4 kV, TEM images were obtained from a Philips TECNAI TEM with an accelerating voltage of 120 kV.

2,3:6,7-Dibenzo-9-oxabicyclo[3.3.1]nona-2,6-diene (1)

A 250 mL flask was flame dried and charged with argon. Phenylacetaldehyde (18.52 g, 0.154 mol) and 100 mL of chloroform (anhydrous) were then added via syringe. The reaction flask was cooled in an ice bath. Trimethylsilyl iodide (25 mL, 37.5 g, 0.188 mol) was added to the solution and the reaction was allowed to stand at 5° C. for 7 days. The reaction was monitored by TLC. After 7 days, sodium thiosulfate (1.0 M, 160 mL) and chloroform (200 mL) were added, and the mixture was stirred until the iodine color was discharged. The organic phase was separated, dried (sodium sulfate), and concentrated in vacuum. Chromatography on silica gel eluting with chloroform yielded 6.1 g of the crystalline ether compound (35%).

3-Hydroxy-2',3',2'',3''-tetramethoxly,-2:5,6-dibenzo-cyclocta-1,5,7-triene (2)

2,3:6,7-Dibenzo-9-oxabicyclo[3.3.1]nona-2,6-diene 1 (2.00 g, 5.84 mmol) in anhydrous THF (60 mL) was placed into a three-necked round bottom flask and cooled in an ice bath under argon. n-butyl lithium (4.92 mL, 2.5 M, 12.4 mmol) was added slowly via syringe. The reaction mixture was stirred at room temperature under argon for 4 h. The reaction was quenched by careful addition of water and extracted with 2×SO mL CHCl$_3$. The combined organic phases were washed with 30 mL of brine, dried over Na$_2$SO$_4$, concentrated under vacuum and purified by column chromatography on silica gel CHCl₃ to yield 1.83 g of 3-Hydroxy-2',3',2",3"-tetramethoxy-2:5,6-dibenzocyclocta-1,5,7-triene (90%).

11,12-Dibromo-5,6,11,12-tetrahydro-dibenzo[a,e]cycloocten-5-ol (3)

Bromine (0.51 mL, 10 mmol) was added dropwise to a stirred solution of 2 (2.22 g, 10 mmol) in CHCl₃ (50 mL). After stirring the mixture for 0.5 h, TLC analysis indicated completion of the reaction. The solvent was evaporated under reduced pressure and the residue was purified by flash chromatography over silica gel (2:1/1:2, v/v, hexanes/CH₂Cl₂) to yield 3 as a light-yellow oil (60%).

5,6-Dihydro-11,12-didehydro-dibenzo[a,e]cycloocten-5-ol (4)

Figure 5:
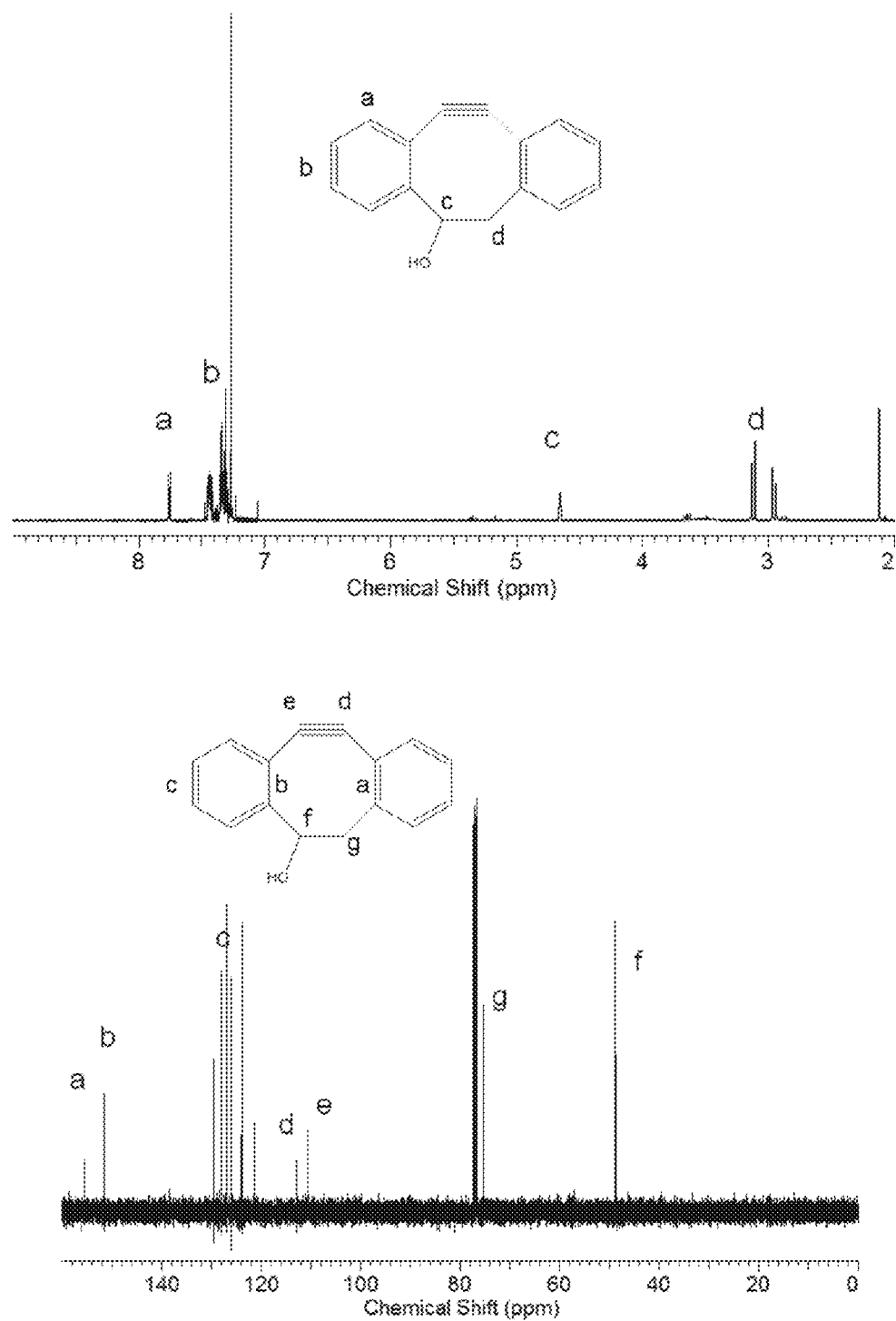
FIG. 5 provides $^1H$ NMR and $^{13}C$ NMR spectra of compound 4 of the reaction scheme of FIG. 1.

Lithium diisopropylamide in tetrahydrofuran (2.0 M; 8.0 mL, 16 mmol) was added dropwise to a stirred solution of 3 (1.53 g, 4.0 mmol) in tetrahydrofuran (40 mL) under an atmosphere of argon. The reaction mixture was stirred for 0.5 h, after which it was quenched by the dropwise addition of water (0.5 mL). The solvents were removed under reduced pressure, and the residue was purified by flash chromatography on silica gel (hexanes/CH₂Cl₂ 2:1/0:1, v/v) to yield 4 as a white amorphous solid (0.52 g, 60%). FIG. 5 provides ¹H NMR and ¹³C NMR spectra of compound 4.

Carbonic acid, 5,6-dihydro-11,12-didehydro-dibenzo[a,e]cycloocten-5-yl ester, 4-nitrophenyl ester (5)

Figure 6:
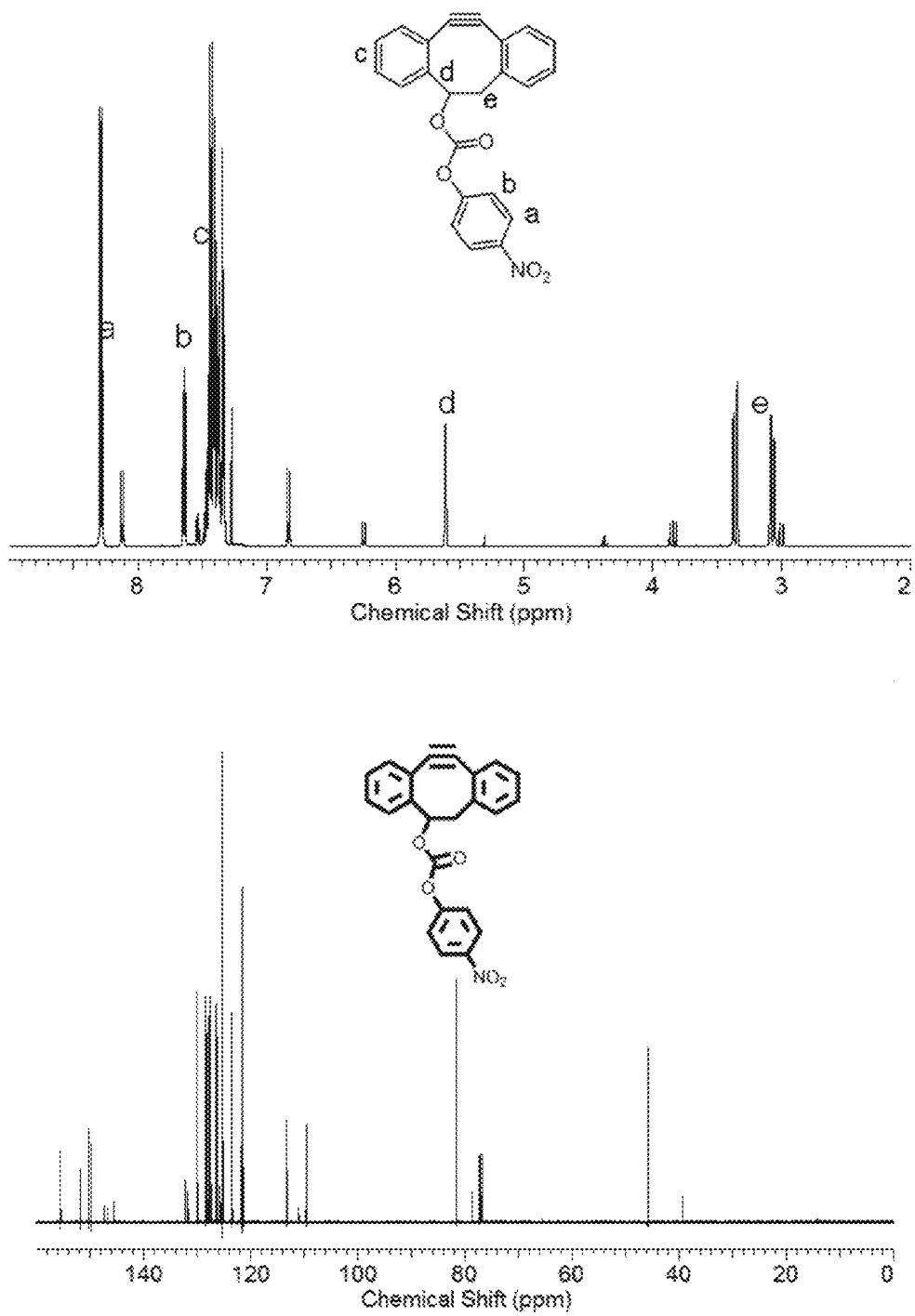
FIG. 6 provides $^1H$ NMR and $^{13}C$ NMR spectra of compound 5 of the reaction scheme of FIG. 1.

4-Nitrophenyl chloroformate (0.4 g, 2 mmol) and pyridine (0.4 mL, 5 mmol) were added to a solution of 4 (0.22 g, 1 mmol) in CH2Cl2 (30 mL). After being stirred for 4 h at room temperature, the mixture was washed with brine (2×10 mL) and the organic layer was dried (MgSO4). The solvents were evaporated under reduced pressure, and the residue was purified by silica gel column chromatography (hexane/ethyl acetate, 10:1, v/v) to afford 5 (0.32 g, 82%). FIG. 6 provides ¹H NMR and ¹³C NMR spectra of compound 5.

6-Aminohexyl-carbamic acid 5,6-dihydro-11,12-didehydrodibenzo[a,e]cycloocten-5-yl ester (6)

Figure 7:
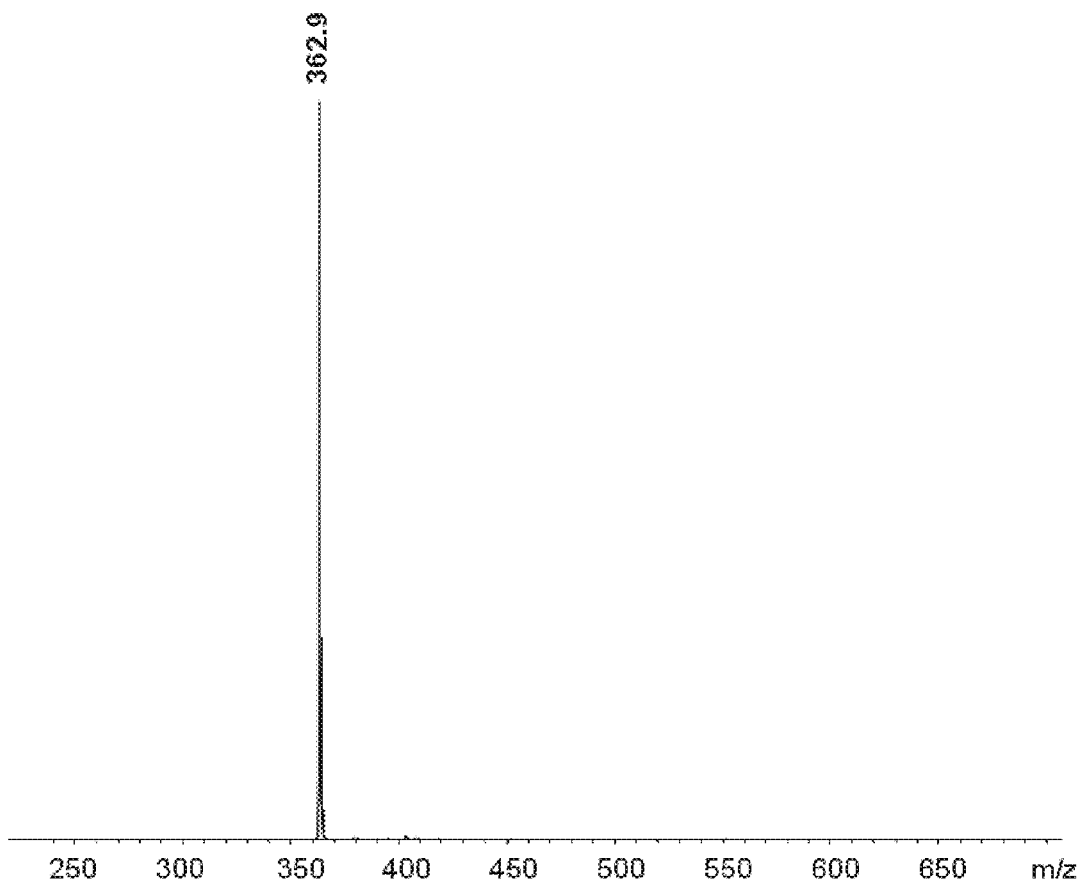
FIG. 7 provides ESI spectra of compound 6 of the reaction scheme of FIG. 1.

To a 50 ml solution of Hexamethylenediamine (151 mg, 1.3 mmol) and 13.2 ul TEA in CH2Cl2 was added 5 (50 mg, 0.26 mmol). After stirring for 3 h, the organic phase was washed with 10×20 ml water, and dried over Na2SO4. Solvent was removed under vacuum and was purified by flash chromatography on silica gel (CH2Cl2/CH3OH, 3:1 with 0.5% isopropylamine) to yield 6 (31 mg, 65%). FIG. 7 provides ESI spectra of compound 6.

Synthesis of DIBO Functionalized Polyγ-Benzyl-L-glutamate

γ-Benzyl-L-glutamate N-carboxyanhydride (Bz-L-GluNCA) and 6 were dissolved in anhydrous DMF in flame dried schlenk flask. After three freeze, pump, thaw cycles the polymerization stood under nitrogen for 3 days. The polymer was precipitated in ethyl ether and dried under vacuum.
Electrospinning
DIBO-PBLG and the unmodified PBLG were both prepared in a 12 wt % 1,4-dioxane solution. Each polymer solution was held in a glass pipette and was electrospun from the orifice with an inner diameter 300 um on the tip. The electric potential was 6 kV over a 22 cm tip-to-collector distance for the modified polymer, and 12 kV over a 27 cm tip-to-collector distance for the unmodified polymer. A proper positive air pressure was applied on the surface of the solution to maintain the feeding rate. Fibers were collected on conductive glass slides for the following fluorescence test, on silicon wafers for SEM observation, and on copper grids for TEM observation. Each kind of collector was placed on top of a large grounded aluminum foil for the collection of electrospinning fibers. Samples were silver coated with an SPI Sputter Coater before the SEM observation.
UV Spectra
UV spectra of DIBO-PBLG before and after electrospinning were measured in DMF solution using a plate reader.

Example 2

4-Dibenzocyclooctynol (DIBO) as an Initiator for poly(ε-caprolactone)

Copper Free Clickable Polymer and Nanofiber-Based Scaffolds

In this work, 4-dibenzocyclooctynol (DIBO) was used to initiate the polymerization of ε-caprolactone (ε-CL). The methodology results in an end-functionalized PCL that is easily functionalized with azide-derivatized compounds under metal-free conditions. This is significant as post synthetic modification and purification of PCL have been limited due to its degradability.

The polymerizations were carried out under traditional Sn-based catalytic conditions using stannous octoate:

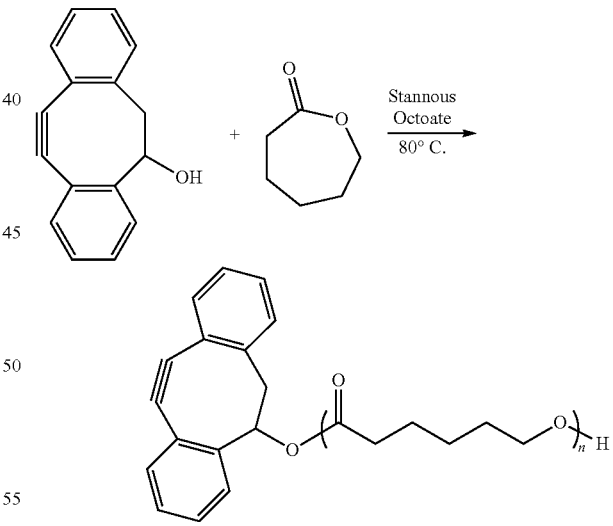

DIBO (28 mg, 0.13 mmol), ε-CL (2.50 g, 21.93 mmol) and freshly distilled stannous octoate (0.053 mmol). Following addition to a flame dried schlenk flask and three cycles of freeze-pump-thaw degassing, the reactions were heated at 80° C. with reaction times that varied from 4 h to 20 h. The polymerization conditions yielded living characteristics with nearly linear increases in molecular mass with time.

Figure 8:
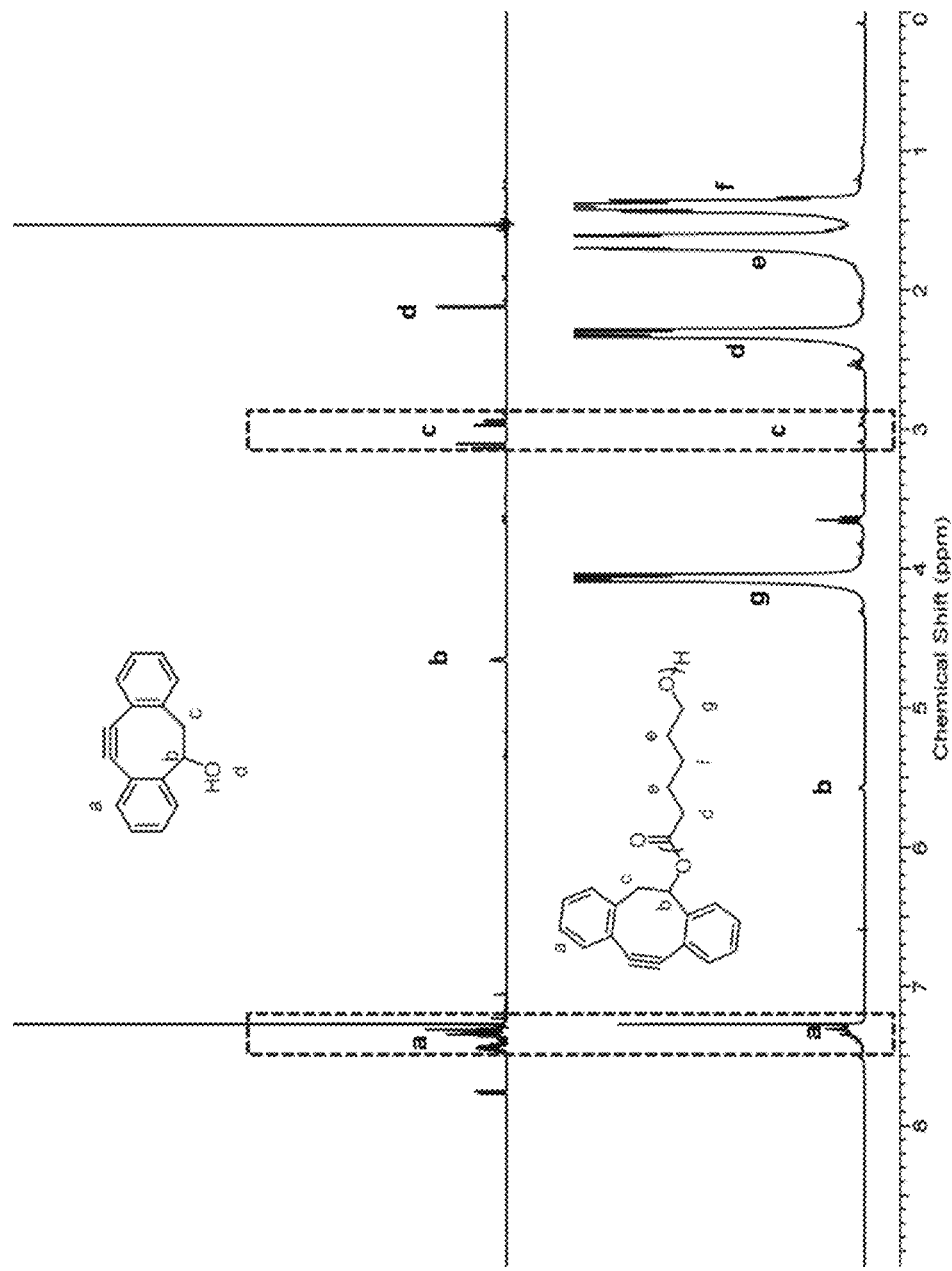
FIG. 8 provides $^1H$ NMR spectra of 4-dibenzocyclooctynol (DIBO) and poly(ε-caprolactone) initiated using DIBO (bottom). The presence and end-functionalization of the DIBO is confirmed via the downfield shift of b from 4.7 to 5.6 ppm.

FIG. 8 shows the 1H NMR spectra of the DIBO initiator (top) and resulting PCL polymer (bottom). The retention of the phenyl resonances (~7.3), the methylene (CH2) from the strained ring (2.9, 3.1) and the downfield shift of b (CHOH) from 4.6 to 5.6 shows that DIBO successfully initiated the polymerization of PCL, and survived intact during the polymerization process. Size exclusion chromatography (SEC) eluograms indicated the molecular mass of DIBO-PCL increased linearly with increased polymerization time from 4 h to 20 h, while the polydispersity remained narrow and mono modal in molecular mass distribution.

The reactivity of the DIBO group at the end of the PCL chain following the polymerization was confirmed using a metal-free click reaction between DIBO and 9-methyleneazidoanthracene. Briefly, DIBO-PCL (Mn=4.5 kDa, 7.7 mg, $1.7\times10^{-3}$ mmol) was added to a 9-methyleneazidoanthracene solution in DMSO (500 µL, $1.4\times10^{-4}$ mmol). After 15 min, the solution was diluted 100 fold and the fluorescence emission spectrum was acquired.

Figure 9:
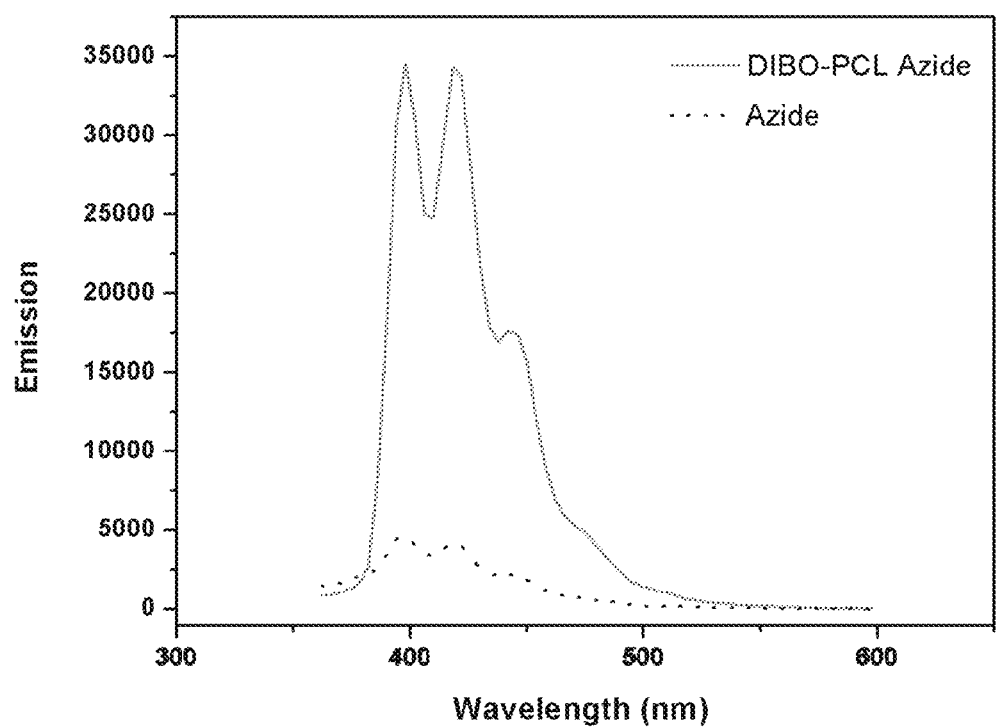
FIG. 9 provides a comparison of fluorescence emission of 9-methyleneazidoanthracene (black) and the DIBO-PCL azide mixture (green).

Following the mixing of the azide solution and the DIBO-PCL solution, a ~7-fold increase in the fluorescence intensity resulted (FIG. 9). A solution of the azide molecule with identical concentration was used as the control.

The DIBO-PCL ($M_n$=20 k) was then used to generate nanofibers via an electrospinning process. A DIBO-PCL solution 40% (wt/mL) in DCM/DMF (4/1) was subjected to well-defined electrospinning conditions of 5.5 kv voltage, and a 10 cm plate height. PCL nanofibers with diameters near 500 nm were successfully obtained using these conditions.

Figure 10:
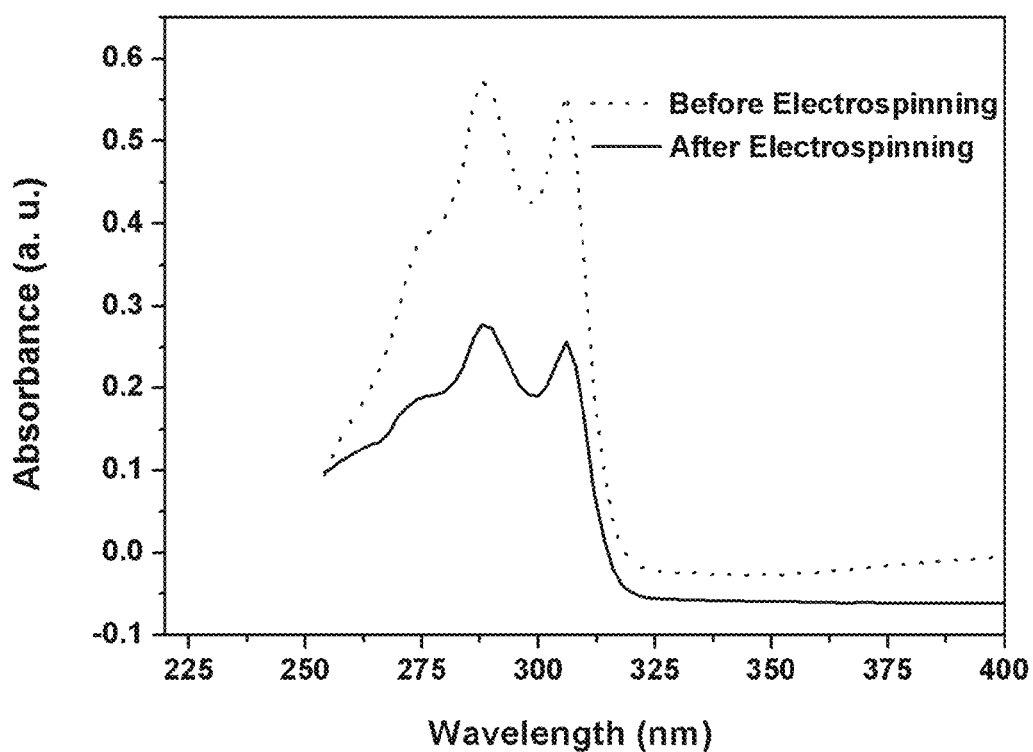
FIG. 10 provides the UV-Visible adsorption spectra of DIBO-PCL before and after electrospinning showing that the strained cyclooctyne survives the electrospinning conditions.

FIG. 10 shows the UV-visible absorption spectra of the DIBO-PCL polymer before and after electrospinning. The π-π* optical transition at 306 nm from the alkyne group did not change position or relative intensity following the electrospinning process, demonstrating that DIBO groups survived.

The reactivity of the DIBO group on the surface of fibers was substantiated using a reaction with an azide-containing fluorescence probe (Chemo 488 azide). A glass slide coated with fibers was immersed in a 0.4% (mg/mL) solution of this fluorescence dye for 5 min at ambient temperature. The glass slide was then washed with water and dried under nitrogen. Fluorescence images of DIBO-PCL nanofibers showed covalent derivatization with 9-methyleneazidoanthracene. The resulting nanofibers are highly fluorescent indicating that DIBO groups are present on the surface of the nanofibers and are able to react with the azide-containing dye. Very little fluorescence was observed in a control experiment using fibers from unmodified PCL under identical conditions indicating nonspecific adsorption of the fluorescence probe is negligible, and the fluorescence is due to the copper-free click reaction between the dye and DIBO group on the surface of the fibers.

4-dibenzocyclooctynol (DIBO) as an initiator for the ring-opening polymerization of ε-caprolactone yielded an DIBO end-functionalized PCL polymer. The DIBO group survives the polymerization conditions and offers efficient, orthogonal and biocompatible functionalization opportunities for both the polymer and polymer-derivatized biomaterials. The combination of PCL and DIBO enables large-scale production of a new type of easily functionalizable nanofiber-based scaffold with versatile regenerative medicine applications.

Methods and Materials

Chemicals and solvents were purchased from either Sigma-Aldrich or Acros and were used without further purification. All reactions were performed in anhydrous conditions under an atmosphere of Argon. Flash chromatography was performed on silica gel (Sorbent Technologies Inc., 70-230 mesh). Stannous octoate (Aldrich) and ε-caprolactone (Acros Organics) were distilled before use.

Size exclusion chromatographic analyses (SEC) were performed using a Waters 150-C Plus instrument equipped with three HR-Styragel columns [100 Å, mixed bed (50/500/103/104 Å), mixed bed (103, 104, 106 Å)], and three detectors including a differential refractometer (Waters 410), a differential viscometer (Viscotek 100), and a laser light scattering detector (Wyatt Technology, DAWN EOS, λ=670 nm). THF was used as eluent with a flow rate of 1.0 mL/min at 30° C. The Molecular weight and polydispersity were calculated according to light scattering data.

$^1$H Nuclear Magnetic Resonance (NMR) spectra was acquired using a Varian Mercury 300 NMR and 500 NMR spectrometer. UV-Vis spectra were measured using a Synergy™ MX plate reader from BioTek. SEM images were acquired using JEOLJSM-7401F with operating voltage as 1 kV. Fluorescence images were acquired using a CKX41 microscope (Olympus, Center Valley, Pa.).

The synthesis of 4-dibenzocyclooctynol (DIBO) has already been experimentally shown in Example 1 and is not repeated here.

Figure 11:
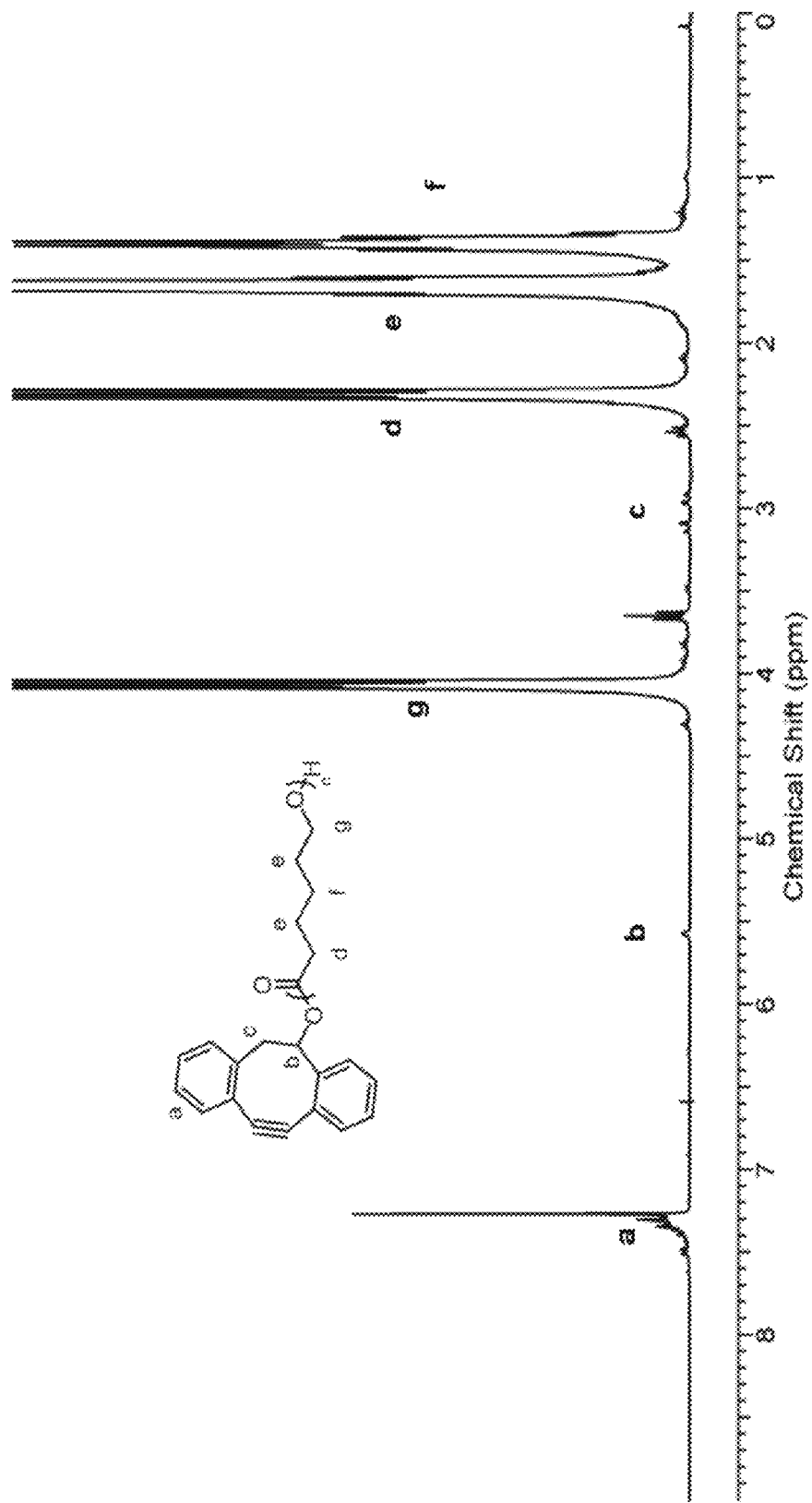
FIG. 11 provides the 1H NMR spectra for the end-functionalized polycaprolactone.

DIBO (28 mg, 0.13 mmol), ε-CL (2.50 g, 21.93 mmol) and freshly distilled stannous octoate (0.053 mmol) were added to a flame dried schlenk flask. After three cycles of freeze-pump-thaw degassing, the reactions were heated at 80° C. with varied reaction times. Following the designated polymerization time, the reaction was quenched in liquid nitrogen, dissolved in THF and precipitated in cold methanol. Molecular Mass, mass distribution, UV visible and NMR spectroscopy were collected as described above. The $^1$H NMR spectra for the end-functionalized PCL is shown in FIG. 11.

Example 3

Directed Differentiation and Neurite Extension of Mouse Embryonic Stem Cell on Aligned Poly(lactide) Nanofibers Functionalized with YIGSR Peptide Here we report a versatile and potentially transformative approach to the creation of nanofeatured poly-L-lactides (PLLAs) capable of being derivatized post-fabrication with any azide functionalized molecule. PLLA is a widely accepted and applied material in regenerative medicine applications, however the creation of suitably functional variants with which to direct cell behavior remains challenging. Electrospinning was used to created nanofiber matrices with fiber diameters near the size of the nanotopography shown to promote stem cell neural differentiation and neurite extension, with functionalization of the scaffolds with the YIGSR peptide undertaken using metal-free alkyne-azide cycloaddition. Such an approach presents a mild and efficient method for the creation of functional scaffolds that avoids PLLA degradation and enables the fabrication of nanofiber mats in a translationally-relevant manner. Herein, we demonstrate the direct differentiation of mouse embryonic stem cells to neural lineages on aligned YIGSR nanofiber matricies in a manner that can readily be scaled and translated to other applications and the clinic.

Materials

Chemicals and solvents were purchased from Sigma-Aldrich were used without further purification unless specifically noted. All reactions were performed in anhydrous conditions under an atmosphere of Argon. Flash chromatography was performed on silica gel (Sorbent Technologies Inc., 70-230 mesh). 9-fluorenylmethoxycarbonyl (Fmoc) protected amino acids, Fmoc-Amino acid loaded-Wang resin and -(1H-Benzotriazol-1-yl)-1,1,3,3-tetramethyluronium hexafluorophosphate (HBTU) were purchased from NovaBiochem. 4-Dibenzyocyclooctynol (DIBO) was synthesized according to previous literature and dried over $P_2O_5$ under vacuum for 72 hours before use (DIBO synthesis in accordance with Ngalle Eric Mbua, J. G., Margreet A. Wolfert, Richard Steet, Geert-Jan Boons chembiochem 2011, 12, 1912-1921; Jung, M. E.; Mossman, A. B.; Lyster, M. A. The Journal of Organic Chemistry 1978, 43, 3698-3701). 1,8-diazabicyclo[5.4.0]undec-7-ene (DBU) was freshly distilled into sealable ampoules from $CaH_2$ under an inert atmosphere. l-Lactide (l-LA, Purac) was first dissolved in methylene chloride, passed through a silica plug and then stirred over anhydrous $MgSO_4$. The solution was then filtered and the methylene chloride removed in vacuo. The resulting solid was taken up in hot toluene before evaporation to dryness in vacuo on a rotary evaporator. The resulting crystalline solid was then transferred to a Schlenk flask and dissolved in anhydrous hot toluene and the solvent was then removed in vacuo on a vacuum manifold. The crystalline white solid was then taken up in anhydrous methylene chloride and transferred by cannula onto activated 3 Å molecular sieves and left to stand for 24 h before being transferred for a second time onto fresh 3 Å sieves for a further 24 h. The methylene chloride/l-LA solution was then transferred to a Schlenk flask using a filter cannula and the methylene chloride removed in vacuo. Finally, the resulting white solid was recrystallised from hot (70° C.) toluene and stored in a glove box at ambient temperature. Deuterated chloroform ($CDCl_3$) was purchased from Apollo Scientific Ltd and distilled from $CaH_2$ before use.

General Considerations

Unless otherwise stated, all manipulations were carried out in a nitrogen filled glove box. $^1H$ and $^{13}C$ NMR spectra were recorded on either a Bruker DPX-400 spectrometer at 298 K. Chemical shifts are reported as δ in parts per million (ppm) and referenced to the chemical shift of the residual solvent resonances ($CHCl_3$: $^1H$ δ=7.26 ppm; $^{13}C$ δ=77.16 ppm). Size exclusion chromatography (SEC) was conducted on Varian GPC 50 instrument fitted with a differential refractive index detector and a mixed-D column set comprising of a short guard column (Varian Polymer Laboratories PLGel 5 μM, 50×7.5 mm) and two further chromatographic columns (Varian Polymer Laboratories PLGel 5 μM, 300×7.5 mm) The mobile phase was $CHCl_3$ (HPLC grade) at a flow rate of 1.0 mL min$^{-1}$ SEC samples were calibrated against Varian Polymer Laboratories Easi-Vials linear poly (styrene) standards (162—2.4×10$^5$ g mol$^{-1}$) using Cirrus v3.3 software.

Typical DIBO-Terminated PLLA Synthesis

In a glove box, 1-LA (2 g, 1.39×10$^{-2}$ mol, 200 eq.) and DIBO (15.3 mg, 6.95×10$^{-5}$ mol, 1 eq.) were added to a glass vial equipped with magnetic stirrer bar and dissolved in methylene chloride (13.9 mL). Under rapid stirring, DBU (21.12 mg, 1.39×10$^{-4}$ mol, 2 eq.) was then added. After 30 min the reaction was quenched by the addition of Dowex 50w ×8 (20-50 mesh) acidic resin followed by precipitation of the polymer into cold hexanes. The precipitate was isolated by filtration before being redissolved in $CHCl_3$ and precipitated a further two times into cold hexanes. The resulting white solid was then subjected to high vacuum for 48 h to remove traces of solvent (1.5 g, 74%). $^1H$ NMR (400 MHz, $CDCl_3$, ppm): δ=7.52 (m, 8H, DIBO $C_6H_4$), 5.59 (s, 1H, CH(OH)), 5.16 (q, 1H, OCH($CH_3$)C(O)), 4.35 (m, 1H, CH($CH_3$)OH), 3.00 (m, 2H, DIBO $CH_2$), 1.58 (d, 3H, OCH($CH_3$)C(O)). $^{13}C$ NMR (100 MHz $CDCl_3$, ppm): δ=169.8, 69.2, 16.8. GPC ($CHCl_3$, poly(styrene) standards): Table 1.

Electrospinning

The DIBO-terminated PLLA (DIBO-PLLA) was dissolved in a 1:4 (v/v) N,N-dimethylformamide/dichloromethane solution to yield a clear, slightly viscous solution of 25% (w/v) concentration. The solution was shaken and left overnight to ensure homogeneity. The solution vial was sealed with Parafilm (Pechiney Plastic Packaging, Chicago, Ill.) to retain the concentration of the solution. The solution was held in a tapered tube made by heating and drawing a glass pipet to an outer diameter of 0.4 mm. The air pressure above the solutions was adjusted to control the flow. The solutions inside the jets were connected to high voltage supplies (0~60 kV, ES60, Gamma High Voltage Research, Ormond Beach, Fla.), and the sample collectors were grounded. A voltage of 12 kV was applied to the DIBO-PLLA solutions, and the tip-to-screen distance was 20 cm. For random fibers, aluminum foil was used as the grounded collector. Round glass cover slides (18 mm diameter, 18 CIR, Fisher Scientific, Pittsburgh, Pa.) were placed on the aluminum foil to collect the fibers. For aligned fibers, a special sheet of stainless steel collector was fabricated and used having elongated openings of 20 mm×70 mm. The aligned fibers were collected on glass coverslips placed in the gaps of the stainless steel collector.

Peptide Synthesis

The Br-GYIGSR was synthesized using standard FMOC conditions on a CEM Discovery microwave peptide synthesizer. The N-terminus was derivatized with 6-Bromohexanoic acid as described previously. Moore, N. M.; Lin, N. J.; Gallant, N. D.; Becker, M. L. Biomaterials 2010, 31, 1604-1611. The crude Br-terminated peptide was purified by reverse phase HPLC. The Br end group was substituted with an azide group in a 1:2 solution of methanol:water containing 18-crown-6 (0.05 eq) stirred at 23° C. overnight. The azide-substituted peptide was purified by dialysis to eliminate the $NaN_3$ residue, and a pale yellow solid was obtained following lyophilization. This substitution was confirmed by ESI-Mass spectra (MW=789.3 Da).

Nanofiber Functionalization

The $N_3$-GYIGSR peptide was dissolved in 1:2 water/methanol (v/v) to yield a 0.5 mg/mL solution. The glass slides covered with electrospun fibers were carefully dipped into the peptide solution three times and rinsed with a 1:2 water/methanol solution. The functionalized fibers were dried overnight and sterilized with ethylene oxide. The sterilized nanofibers were degassed for 3 days.

Lowry Assay

YIGSR concentration on the fiber was determined using the Lowry assay as previously described. Miller, J. S.; Shen, C. J.; Legant, W. R.; Baranski, J. D.; Blakely, B. L.; Chen, C. S. Biomaterials 2010, 31, 3736-3743. Briefly, 1.0 mg peptide functionalized polymer was dissolved in 1.000 mL of DMSO. A standard curve was created by dissolving 1 ug/mL, 2 ug/mL, 5 ug/mL, 10 ug/mL or 20 ug/mL of YIGSR peptide in DMSO containing with 1.0 mg of polymer per mL. Total protein within each sample was measured using a Dc Protein assay (Biorad, Hercules, Calif.) according to manufacture protocol.

Scanning Electron Microscopy

The fiber dimensions and alignment were evaluated by SEM (JSM-7401F, JEOL, Peabody, Mass.). The acceleration voltage was set at 1 kV. The fibers were not sputter coated prior to imaging. The fiber diameters and angles were calculated by measuring over 100 fibers using Image J.

D3 Mouse Embryonic Stem Cell Culture and Seeding

D3 mouse ESC [Doetschman, T.; Eistetter, H.; Katz, M.; Schmidt, W.; Kemler, R. J Embryol Exp Mophol 1985, 87, 27-45] were cultured on 0.1% gelatin-coated tissue culture flasks in ESC media (DMEM supplemented with 10% FBS, $10^{-4}$M β-mercaptoethanol, 0.224 µg/mL L-glutamine, 1.33 µg/mL HEPES, and 1,000 units/mL human recombinant LIF). Nanofiber-loaded coverslips were placed in a 12 well plate, sterilized with ethylene oxide and then wet with 80% F-12/20% Neurobasal media (Invitrogen, Grand Island, N.Y.) for 1 h. D3 cells (325,000) were seeded evenly on each sample in 400 µL of fresh neural media (80% F-12/20% Neurobasal media with N2 and B27 supplements, 10 mM sodium pyruvate and 1 µM retinoic acid). The media was changed every other day for the duration of the experiment.

Immunofluorescence and Alkaline Phosphatase Quantification

Immunofluorescence was conducted as previously described. Smith Callahan, L. A.; Ma, Y.; Stafford, C. M.; Becker, M. L. Biomaterials Science 2013. Briefly, cells cultured on nanofiber-coated coverslips were fixed at designated time points with 4% paraformaldehyde/PBS, washed, and stored at 4° C. in PBS. Nonspecific antibody binding was blocked by incubating in 10% goat serum, then the gradients were exposed to Neuron-specific class III beta-tubulin (TUJ1) (PRB-435p, Covance, 1:500), followed by appropriate secondary antibody conjugated with Alexaflour 544 (Invitrogen). DAPI was used to stain the cell nuclei. Images were taken with an automated IX81 microscope (Olympus). Cellular density at each position was determined by using the automated counting function of ImageJ to count nuclei in images at each position from at least 5 separate samples. Statistical averages of neurite lengths from the nucleus were made from measurements of at least 250 cells from at least 3 separate samples per group using ImageJ (National Institute of Health, Bethesda, Md., USA). Fraction of cells expressing TUJ1 was determined using the ImageJ cell counter and dividing the total number of cells expressing TUJ1 staining by the number of nuclei in at least 10 fields of view per sample and 1000 cells per sample group at each time point. Quantification of alkaline phosphatase was determined with a SensoLyte pNNP Alkaline Phosphatase assay kit (AnaSpec, Fremont, Calif.) according to the manufacturer's protocol. For normalization, total protein was measured in samples with a Dc Protein assay (Biorad, Hercules, Calif.) according to the manufacturer's protocol.

Semi-Quantitative PCR

Total RNA was isolated from at least three replicates using an RNeasy Mini Kit (Qiagen, Hilden, Germany) according to the manufacturer's protocol after cells were harvested from material samples with a cell scraper. RNA samples with an optical density ratio of absorbance at 260 nm (RNA) over that at 280 nm (protein) greater than 1.9 were used to make cDNA. Based on the absorbance reading at 260 nm, 0.5 mg of RNA from each sample was used to make cDNA using a 2710 thermal cycler (Applied Biosystems) with TaqMan reverse transcription reagents. The thermocycler program was as follows: 10 min incubation at 25° C., 30 min reverse transcription at 48° C., and 5 min inactivation at 95° C. Two microliters of each reaction was subject to PCR using AmpliTaq Gold DNA polymerase (Applied Biosystems) for each of the following:

Nanog (5'-agggtctgctactgagatgctctg-3' and 5'-atcttctgatcctggcaag-3'); Oct 3/4 (5'-ggggatccgatggcatactgtggacctcag-3' and 5'-ggggaattcgcttcgggcacttcagaaac-3'); pax6 (5'-aagggcggtgagcagatgt-3' and 5'-gcatgctggagctggtttgg-3'); Nestin (5'-gtgcctctggatgatg-3' and 5'-ttgaccttcctccccctc-3'); TUJ1 (5'-tcactgtgcctgaacttacc-3' and 5'-ggaacatagccgtaaactgc-3'); Microtubule-associated protein 2 (MAP2) (5'-gaggcagaagctccaaga-3' and 5'-ctggacccactccacaaact-3'); Oligodendrocyte transcription factor 1 (OLIG1) (5'-tgcgcgcgagaaggccgaag-3' and 5'-cccagccagccctcacttg-3'); Glial fibrillary acidic protein (GFAP) (5'-gaggcagaagctccaaga-3' and 5'-gctctagggactcgttcgtg-3'); Glyceraldehyde 3-phosphate dehydrogenase (GAPDH) (5'-accacagtccatgccatcac-3' and 5'-tccaccaccctgttgctgta-3').

The cycling conditions were 94° C. for 5 min followed by 94° C. for 30 s, 55° C. for 60 s, 72° C. for 60 sec for Nanog and Oct 3/4, 94° C. for 30 sec, 55° C. for 30 sec, 72° C. for 60 sec for pax6 and TUJ1; 94° C. for 30 sec, 55° C. for 30 sec, 72° C. for 45 sec for Nestin; 94° C. for 30 sec, 56° C. for 30 sec, 72° C. for 60 sec for GFAP and OLIGO1; and 94° C. for 30 sec, 62° C. for 30 sec, 72° C. for 60 sec for GAPDH. All amplifications were run for 35 cycles and followed by a 10 min extension at 72° C. The PCR product was loaded in a 1% agarose gel stained with ethidium bromide and run for 45 min at 100 V. Fluorescent images of gels were obtained with a Biospectrum Imaging System (UVP, Upland, Calif.). The relative densities of the bands were analyzed with VisionWorks LS (UVP) and normalized to GAPDH density for the sample.

Statistics

All experiments were conducted at least 3 times (n≥3) with multiple substrates as noted in each section. All quantitative data are presented as the average±standard deviation. One-way analysis of variance (ANOVA) with Tukey post hoc analysis was performed where applicable. Significance was set at a p-value of less than 0.05.

Results

Synthesis of end-functional poly(L-lactide)s, PLLAs, was undertaken by the ring-opening polymerization of L-lactide catalyzed by 1,8-diazabicyclo[5.4.0]undec-7-ene (DBU) using 4-dibenzyocyclooctynol (DIBO) as the initiator, as follows:

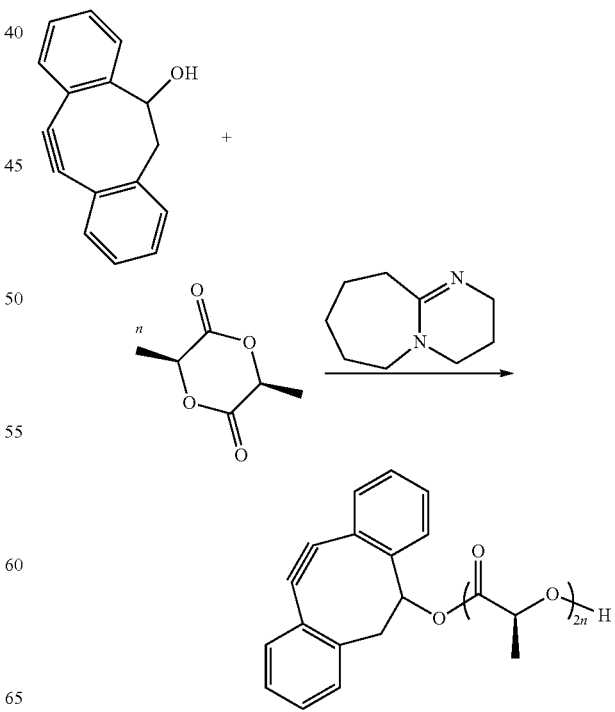

This technique simplifies the removal of catalytic residues and enables the targeting of high molecular weight PLLAs with high end group fidelity. PLLAs with targeted degrees of polymerization of 170, 200 and 370 were obtained within 30 min and yielded polymers of 41.1, 59.5 and 87.4 kDa with narrow molar mass distributions ($Đ_M$<1.13).

Nanofibrous matrices, which emulate the size scale of the native ECM, were shown to promote cellular attachment, proliferation and differentiation more effectively than traditional tissue engineering matrices. Electrospinning is one method capable of generating nanofibers on the size scale of ECM. Using DIBO-PLLA, both random and aligned fibers were fabricated; the average fiber diameter was 345 nm±51 nm and 338 nm±63 nm, respectively. The aligned matrices possessed high degree of alignment with a narrow angular distribution of oriented fibers ~89.5°±6.5°. Functionalized nanofibers were found to have 4.94 μg±2.76 μg (average±standard deviation) of YIGSR peptide per 1000 μg of functionalized fiber.

TABLE 1

Summary of size exclusion chromatography results for synthesized 4-dibenzocyclooctynol (DIBO) terminated-L-lactide

| Sample | [M]/[I] | DP  | $M_n$ (Da) | $(M_w)$ | $Đ_M$ |
|--------|---------|-----|------------|---------|-------|
| 1      | 175     | 170 | 41 100     | 43 500  | 1.06  |
| 2      | 350     | 200 | 59 500     | 67 500  | 1.13  |
| 3      | 450     | 370 | 87 400     | 90 200  | 1.03  |

Fiber diameter, alignment and functionalization can affect neural progenitor differentiation and neurite extension5,6, 28-30. A significantly higher fraction of ESC cultured on aligned functionalized samples (0.75±0.07 (average±standard deviation)) compared to ESC cultured on both the random unfunctionalized (0.53±0.03; p-value=0.001) and functionalized samples (0.53±0.02; p-value=0.001) expressed TUJ1 after 1 day of differentiation, while ESC cultured on the aligned unfunctionalized samples expressed an intermediate fraction TUJ1 (0.63±0.03). After 3 days of differentiation, a significantly higher fraction of ESC cultured on aligned functionalized samples (0.71±0.01) expressed TUJ1 compared to ESC cultured on the random unfunctionalized (0.56±0.01, p-value=0.04). The random functionalized (0.61±0.01) and aligned unfunctionalized (0.61±0.08) expressed intermediate fractional values. Previous studies on the effects of fiber alignment on stem cell differentiation to neural lineages have diverged with some indicating similarity to our results or others indicating that alignment does not affect the fraction of cells expressing TUJ1. Differences between cell lines and differentiation protocols, especially temporally, most likely contribute to this discrepancy. Average neurite length of ESC cultured on aligned functionalized samples was significantly longer than that of ESC cultured on both the random unfunctionalized and unfunctionalized samples. The results are similar to previous studies that have found fiber alignment and the incorporation of YIGSR improved neurite extension compared to control. Subtle differences in cell density are unlikely to impact these results since a similar amount of DNA was isolated from all sample groups at each time point studied (data not shown). However, fiber density cannot be controlled precisely between samples and may contribute to differences between groups.

Figure 12:
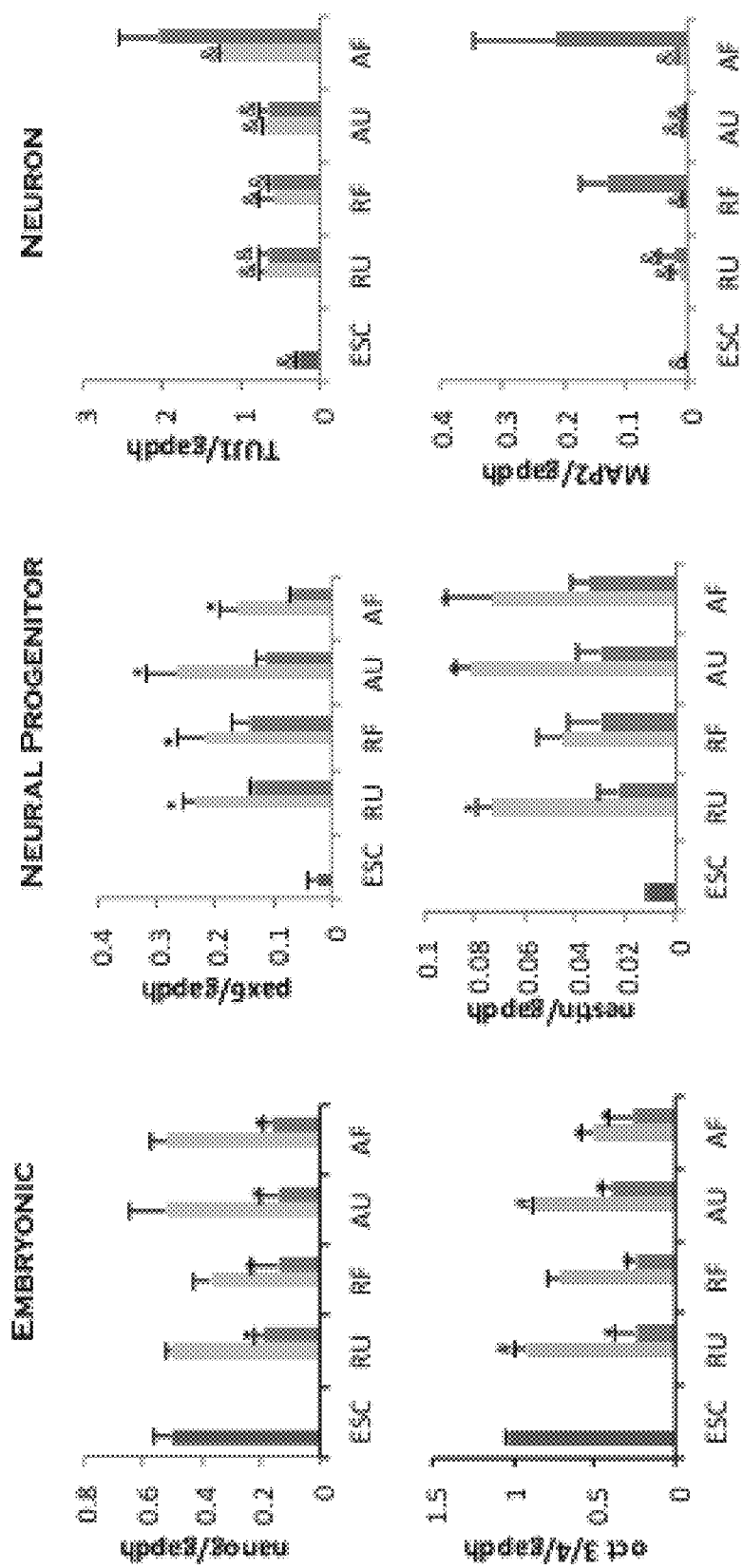
FIG. 12 provides graphs showing the influence of nanofiber alignment and YIGSR functionalization on differentiating mouse embryonic stem cells embryonic (nanog and oct3/4), neural progenitor (pax6 and nestin), and neural (neuron-specific class III beta-tubulin (TUJ1) and Microtubule-associated protein 2 (MAP2)) gene expression over 3 days of culture. Sample groups include embryonic stem cells (ESC), random unfunctionalized (RU), random YIGSR functionalized (RF), aligned unfunctionalized (AU) and aligned YIGSR functionalized (AF). The use of * indicates a p-value<0.05 relative to ESC. The use of # indicates a p-value<0.05 relative to 1 day aligned YIGSR functionalized sample. The use of & indicates a p-value<0.05 relative to 3 day aligned YIGSR functionalized sample.

Gene expression for embryonic stem cell markers, nanog and Oct 3/4, was higher in the starting ESC population and decreased with increased exposure to neural differentiation media in ESC in all sample groups. In combination with alkaline phosphatase quantification which decreased relative to the total protein of each sample over time (data not shown) indicates that all sample groups support ESC differentiation. Although all sample groups supported ESC differentiation, ESC on the aligned functionalized samples showed a significant decrease of Oct 3/4 mRNA expression compared to the ESC starting population after 1 day, while the ESC on the other groups required 3 days of culture show a significant decrease in Oct 3/4 mRNA expression relative to the ESC starting population. PAX6 mRNA expression, a neural progenitor marker, was up regulated in ESC on all sample groups compared to the ESC starting population after 1 day of differentiation (FIG. 12). Similarly, nestin mRNA expression, another neural progenitor marker, was found to be up regulated after 1 day of neural differentiation in ESC cultured on random unfunctionalized, aligned unfunctionalized, and aligned functionalized samples compared to the ESC starting population (FIG. 12). After 3 days of neural culture, mRNA expression of both pax6 and nestin decreased in ESC on all sample groups indicating differentiation of the ESC beyond neural progenitors. After 3 days of differentiation, mRNA expression of TUJ1, an immature neuron marker, was significantly increased in ESC cultured on the aligned functionalized samples compared to ESC cultured on the other sample groups (FIG. 12). MAP2 mRNA expression, a mature neuron marker, was also up regulated in ESC cultured on aligned functionalized samples after 3 days of differentiation compared to ESC cultured on the unfunctionalized random and aligned samples (FIG. 12). GFAP, an astrocyte marker and Oligo1, an oligodendrocyte marker, were not detectable by PCR in ESC cultured on any of the sample groups indicating that those cell types were not yet present in the cultures (data not shown). While fiber alignment has been shown to effect gene expression in stem cells, studies examining the effects of fiber-aligned or YIGSR peptide-functionalized mats on the gene expression of ESC undergoing neural differentiation could not be located in the literature.

Conclusions

Synthetic polymers functionalized with biological moieties have widespread applications in clinical regenerative medicine. Through the end-functionalization of PLLA with DIBO, a method has been developed for the facile, post-fabrication functionalization of tissue engineering matrices in a translationally-relevant manner. Increased neurite length and neural gene expression of ESC cultured on functionalized matrices compared to gene expression of ESC cultured on unfunctionalized matrices indicated the functionalization is bioavailable to the cells and DIBO PLLA offers a clinically relevant material for the production of functional synthetic polymers. The post-fabrication strategy we demonstrate herein is a transformative approach to medical ideas and innovations that many have ignored clinically due to characterization challenges, difficulty of processing bioactive species and concerns about regulatory pathways for combination products.

Example 4

One Batch Difunctionalization of Poly (ε-caprolactone) Copolymer Derivatized Nanofiber Scaffold with Strain-Promoted Azide Alkyne Cycloaddition and Oxime Chemistry In this paper, two orthogonal chemical reactions, copper-free click chemistry and oxime reaction are combined to generate an efficient, biocompatible one batch method of difunctionalized nanofiber based scaffolds. DIBO was used as the initiator for the ring-opening copolymerization of ε-caprolactone and 1,4,8-trioxaspiro[4.6]-9-undecanone (TOSUO) to yield the DIBO-(P(CL-co-OPD)). Post-polymerization deprotection proceeded under mild condition to recover the reactive ketone group. Further di-functionalization of the polymer was carried out using azide terminated PEG and O-(pent-4-en-1-yl)hydroxylamine hydrochloride in one batch. The feasibility of easy functionalization of nanofiber based scaffold is also substantiated with fluorescence probes Chemo 488 azide (green) and Alexa Fluor 568 hydrazide (red).

General Methods and Materials

All chemicals and solvents were purchased from Sigma-Aldrich or Acros and were used without further purification unless otherwise noted. All reactions were performed in anhydrous conditions under an atmosphere of Argon. Flash chromatography was performed on silica gel (Sorbent Technologies Inc., 70-230 mesh). Stannous octoate (Aldrich) and ε-caprolactone (Acros Organics) were distilled prior to use. 4-dibenzocyclooctynol (DIBO) was synthesized according to methods described previously.[26,35] Chemo 488 azide was acquired from Active Motif and Alexa Fluor 568 was acquired from Life Technologies.

Instrument Information

Size exclusion chromatographic analyses (SEC) were performed using a Waters 150-C Plus instrument equipped with three HR-Styragel columns [100 Å, mixed bed (50/500/103/104 Å), mixed bed (103, 104, 106 Å)], and three detectors including a differential refractometer (Waters 410), a differential viscometer (Viscotek 100), and a laser light scattering detector (Wyatt Technology, DAWN EOS, λ=670 nm). THF was used as eluent with a flow rate of 1.00 mL/min at 30° C. The molecular mass and molecular mass distribution were calculated from light scattering data.

$^1$H Nuclear Magnetic Resonance (NMR) spectra were acquired on Varian Mercury 300 NMR or 500 NMR spectrometers. UV-Vis spectra were measured using a Synergy™ MX Plate Reader From BioTek.

Fluorescence images were acquired using an inverted IX81. Scanning electron microscopy (SEM) images were acquired using JEOL-JSM-7401F with operating voltage as 1 kV.

Synthesis of the Monomer
1,4,8-trioxaspiro[4.6]-9-undecanone (TOSUO)

This monomer was synthesized according to known methods described previously. Tian, D.; Dubois, P.; Grandfils, C.; Jérôme, R. Macromolecules 1997, 30, 406.

Figure 14:
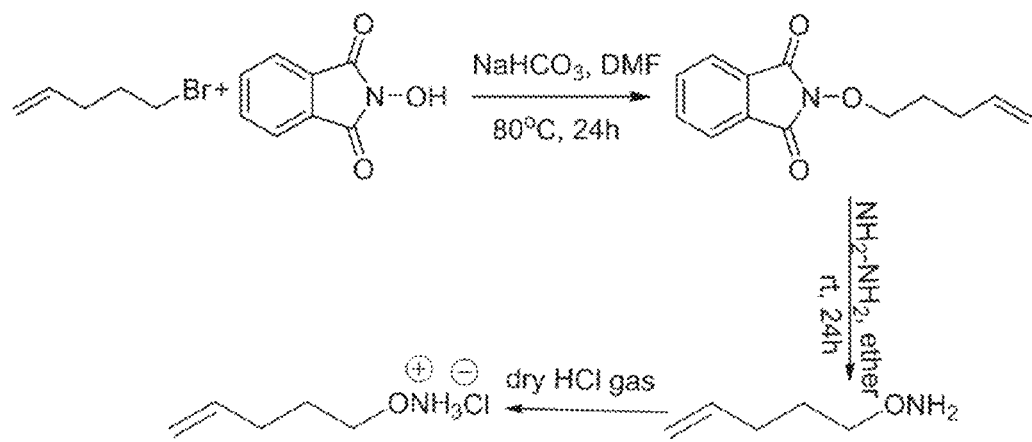
FIG. 14 provides the reaction scheme for the synthesis of O-(pent-4-en-1-yl)hydroxylamine hydrochloride.
Figure 15:
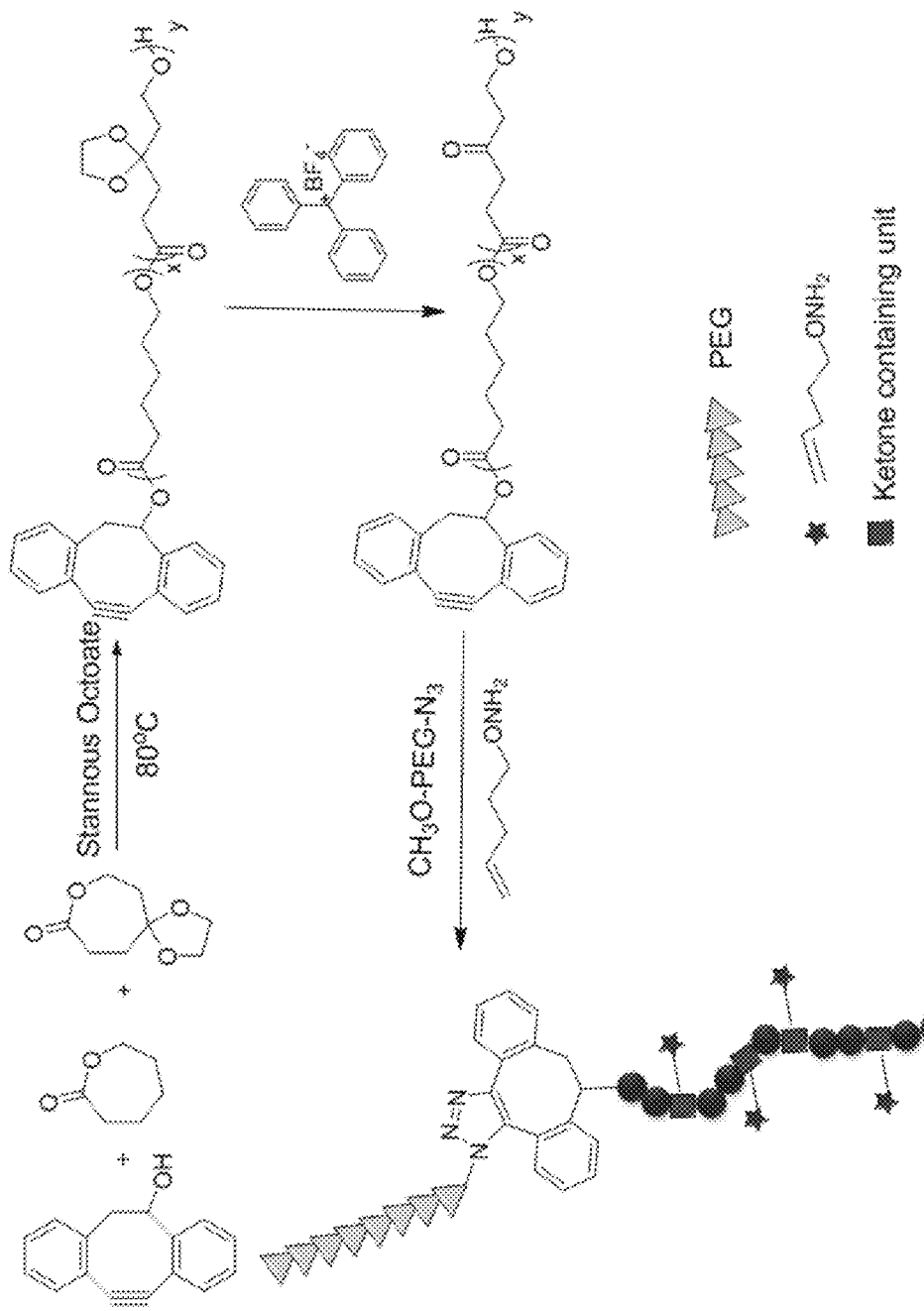
FIG. 15 provides the reaction scheme for the synthesis for the di-functionalized polymer in one batch with copper-free click chemistry and oxime ligation.

Synthesis of O-(pent-4-en-1-yl)hydroxylamine hydrochloride (FIG. 14)

5-Bromo-1-pentene (3 g, 20 mmol, 1 eq.), N-hydroxyphthalimide (5 g, 30 mmol, 1.5 eq) and NaHCO$_3$ (3.2 g, 30 mmol, 1.5 eq.) were suspended in 100 mL THF. The deep red reaction system was refluxed at 80° C. for 24 h with magnetic stirring. Solvent was removed under reduced pressure, and the solid residue was redissolved in 200 mL CHCl$_3$. This solution was washed with saturated sodium carbonate solution until the aqueous phase was colorless. The organic phase was collected and dried with MgSO$_4$ and then evaporated under reduced pressure. The crude product was purified by flash column chromatography on silica gel to afford the product as a white solid (3.4 g, yield 75%). The product from previous step (2.3 g, 10 mmol, 1 eq.) and hydrazine monohydrate (1 mL, 20 mmol, 1.5 eq.) were added into 100 mL of diethyl ether. The suspension was stirred at ambient temperature for 24 h, and then filtered to remove the solid byproduct. The collected organic phase was dried over MgSO$_4$. After acidification with dry HCl gas, the product was afforded as a white solid. (1.3 g, yield 92%). The product was confirmed by $^1$H NMR and $^{13}$C NMR spectra.

Synthesis of DIBO Terminated Copolymer

DIBO (28.0 mg, 0.13 mmol), -caprolactone (2.50 g, 21.9 mmol) 1,4,8-trioxaspiro[4.6]-9-undecanone (TOSUO) (138.0 mg, 0.80 mmol) and freshly distilled stannous octoate (0.053 mmol) were added to a flame dried schlenk flask. After three cycles of freeze-pump-thaw degassing, the reactions were heated at 80° C. for 24 h. The product was confirmed by $^1$H NMR spectroscopy, UV-vis spectroscopy and SEC.

Recovery of Reactive Ketone Group

Triphenylcarbenium tetrafluoroborate (235 mg, 71 mmol) was added to the polymer solution (470 mg/14 mL), after 2 h under the protection of argon, the product was obtained by precipitating in cold methanol. The product was confirmed by $^1$H NMR spectra and UV-vis spectra.

One Batch Di-Functionalization of the Polymer

CH$_3$O-PEG-N$_3$ (Mn=1 k, 5 mg, 0.005 mmol, 2 eq), O-(pent-4-en-1-yl)hydroxylamine hydrochloride (12 mg, 87 mmol, 2 eq), triethylamine (9.5 μL, 68 mmol, 1.5 eq) and 4-methylbenzenesulfonic acid (2 mg) were added to deprotected polymer in THF solution (50/3 mg/mL). After 5 h, the solid was removed by centrifuge and product was recovered by precipitating in cold methanol. The product was confirmed by $^1$H NMR spectra.

Electrospinning

Electrospinning was conducted under 10 kv, 10 cm tip-receiver height with 40% (w/v) solution in 4:1 DCM/DMF. SEM images were acquired using JEOLJSM-7401F with operating voltage as 1 kV.

UV-Vis Spectroscopy.

UV-vis spectra of DIBO-P(CL-co-OPD)), deprotected copolymer and nanofiber obtained from electrospinning were measured to ensure the survival of DIBO group from polymerization, deprotection reaction and electrospinning respectively.

One Batch Di-Functionalization of Nanofiber Scaffold

The glass slides with deposited nanofibers were immersed in the solution of Chemo 488 azide (0.4% mg/mL) and Alexa Fluor 568 (0.2% mg/mL, with 2 mg 4-methylbenzenesulfonic as catalyst) for 5 min. After the glass slide was removed, it was washed with water and methanol. FITC and TRITC modes were used to image the fluorescence of resulted fibers. Control experiments to remove the effect of physical adsorption of fluorescence probe were carried out with nanofibers generated from unmodified PCL.

Polymerization and Deprotection $^1$H NMR spectra indicates DIBO survived the polymerization process and initiated the polymerization in accordance with previous results. According to SEC results, the molecular weight of the yielded polymer is about Mn=19 k with PDI around 1.23. The content of the OPD monomer is calculated to be about 10% according to the integration of peak δ=2.0. Recovery of ketone group after polymerization was achieved with triphenylcarbenium tetrafluoroborate. The OCH$_2$CH$_2$O peak in the $^1$H NMR disappeared and the CH₂ adjacent to ketone group shifted to two peaks yielding evidence for successful deprotection.

The UV-vis absorption peak of the alkyne in DIBO at about 306 nm is characteristic for DIBO functional group, which has been used for reaction kinetic study of DIBO with azide. UV-vis spectra was used to verify the existence of DIBO group. The UV-vis spectrum demonstrated that the polymer obtained from polymerization had the π-π* optical transition at 306 nm from the alkyne characteristic of the DIBO group. This means again the DIBO group survived the polymerization, which is in accordance with previous result. After deprotection to recover the ketone group, the polymer was measured again by UV-vis spectra to see whether DIBO is still intact, and the 306 nm peak indicates that the DIBO is still in the polymer after the deprotection reaction.

One Batch Di-Functionalization of the Copolymer

A change of the chemical shift regime δ=2.5-2.7 also indicated the one batch di-functionalization happened successfully. So in this case, we synthesized a biocompatible and biodegradable PCL based copolymer available for easy di-functionalization in one batch.

Nanofiber Based Scaffold Fabrication

Figure 13:
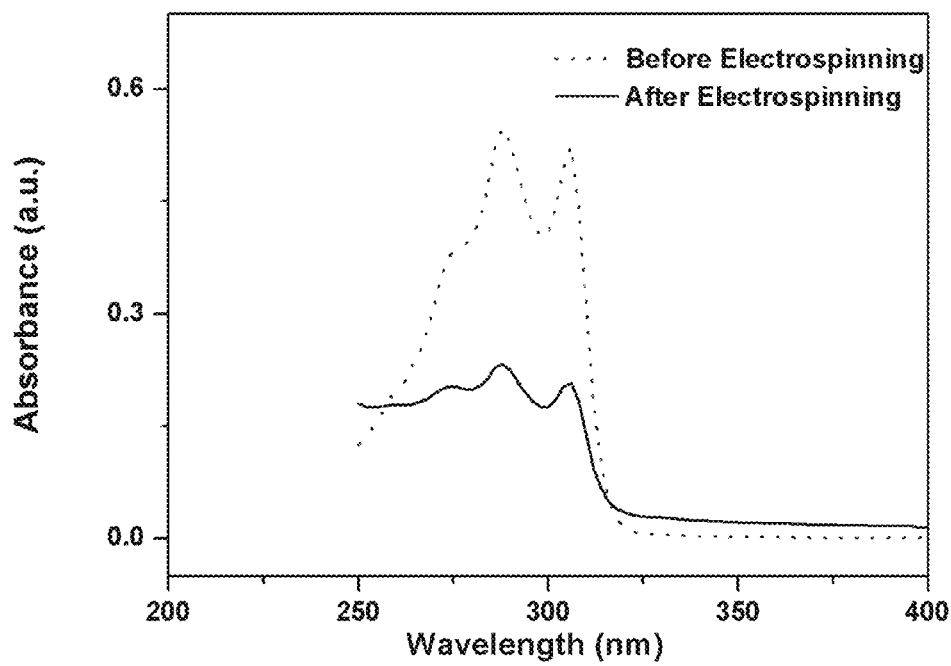
FIG. 13 provides UV-vis spectra of polymer before electrospinning and after electrospinning, proving the survival of DIBO group in electrospinning.

SEM measurements were conducted after electrospinning to image the morphology of the obtained fibers. According to SEM image, we generated nanofibers with diameter around 600 nm. To check the viability of DIBO group, UV-vis measurement is used. FIG. 13 indicates that there is no change to the 306 nm peak in the absorbance before and after electrospinning. So again we proved that the DIBO group survived the process of electrospinning.

Di-Functionalization of the Scaffold

A green fluorescence was detected under FITC mode proving that the copper-free click reaction happened at the surface of nanofibers, which is in accordance with previous research. While keeping the sample and settings in microscope unchanged, just switching from FITC to TRITC mode, red fluorescence was also observed. This result substantiates the oxime reaction is also successful on the surface of nanofibers. With consideration to the control experiment, little fluorescence was observed which could be due to physical adsorption of the fluorescence probe. The physical adsorption of fluorescence probe is negligible and the fluorescence on the surface of fibers is due to the covalent conjugation of fluorescence molecules and the surface reactive sites. The fluorescence images demonstrate the nanofibers are di-functionalized using two efficient orthogonal reactions.

This manuscript describes the synthesis of a P(CL-co-OPD) copolymer with end-capped DIBO group. Successful post-polymerization modification recovers the reactive ketone group for oxime ligation while keeping the DIBO group intact. One batch di-functionalization works for both the polymer and polymer derivatized nanofiber which were characterized with ¹H NMR and fluorescence. The methodology described in this paper offers potential applications for efficient, orthogonal and biocompatible functionalization of tissue engineering scaffolds with two types or even more of bioactive molecules. This research provides versatile approaches to highly functionalized scaffold for regenerative medicine applications.

What is claimed is:

1. A method of constructing biocompatible polymeric structures comprising the steps of:
    preparing a biocompatible polymer including a strained cycloalkyne end group by ring-opening polymerization of one or more monomers employing a ROP initiator having a strained cycloalkyne;
    forming a polymeric structure from the biocompatible polymer such that the strained cycloalkyne end group remains on the biocompatible polymer;
    providing an azide tethered molecule; and, after said step of forming,
    reacting the azide tethered molecule with the cycloalkyne in an azide alkyne cycloaddition reaction to further functionalize the polymeric structure.

2. The method of claim 1, wherein the ROP initiator includes a five to nine member strained cycloalkyne.

3. The method of claim 2, wherein the ROP initiator further includes a reactive group selected from a hydroxyl group or an amine group.

4. The method of claim 3, wherein the reactive group is an hydroxyl group, and the one or more monomers polymerized in said step of polymerizing are cyclic esters.

5. The method of claim 3, wherein the reactive group is an hydroxyl group, and the one or more monomers polymerized in said step of polymerizing are selected from lactones, lactides and glycolides.

6. The method of claim 3, wherein the reactive group is an amine, and the one or more monomers polymerized in said step of polymerization are N-carb oxylic anhydrides.

7. The method of claim 3, wherein the ROP initiator includes an 8-member cycloalkyne.

8. The method of claim 7, wherein the ROP initiator is selected according to the following structure:

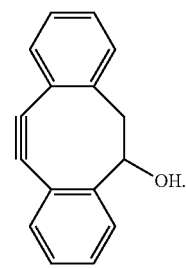

9. The method of claim 7, wherein the ROP initiator is selected according to the following structure:

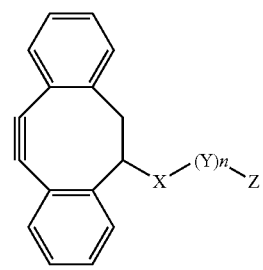

wherein X is a urethane or carbonate, Y is methylene (CH2) group or ethoxy (CH₂CH₂O) group, n is from 1 or more to 12 or less, and Z is an amine or hydroxyl or hydroxyethyl.

10. The method of claim 7, wherein the ROP initiator is selected according to the following structure:

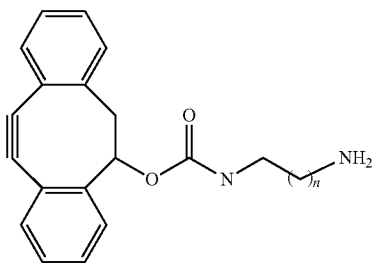

wherein n is from 1 to 5.

11. The method of claim 7, wherein the ROP initiator is selected according to the following structure:

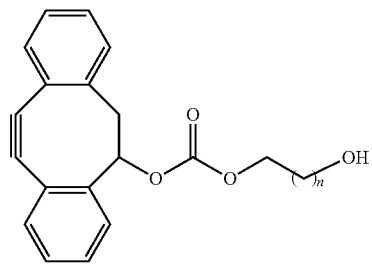

wherein n is from 1 to 11.

12. The method of claim 7, wherein the ROP initiator is selected according to the following structure:

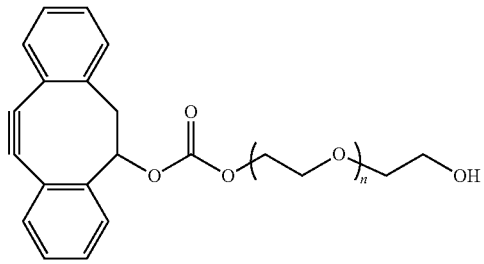

wherein n is from 1 to 5.

13. The method of claim 1, wherein said step of forming a polymeric structure includes forming said polymeric structure from said biocompatible polymer using a process selected from the group consisting of electrospinning, melt-blowing, salt leach scaffolding, nanofibers by gas jet, ink jet printing and 3d printing.

14. The method of claim 12, wherein the strained cycloalkyne is present on said polymeric structure and will bind with said azide tethered molecule after said step of forming.

15. The method of claim 14, further including the step of storing the polymeric structure after said step of forming so as to preserve the strained cycloalkyne end group for future use, and performing said step of reacting an azide tethered molecule after said step of storing such that the further functionalization of said step of reacting is carried out as functionalization is needed and such functionalization can be tailored to a desired functionality.

16. The method of claim 15, wherein the azide-functionalized group is selected from the group consisting of azide-functionalized DNA, azide-functionalized peptides, azide-functionalized proteins, azide-functionalized sugars, azide-functionalized metal, azide-functionalized nanoparticles and azide-functionalized antimicrobials.

17. A ring opening polymerization initiator according to the following structures:

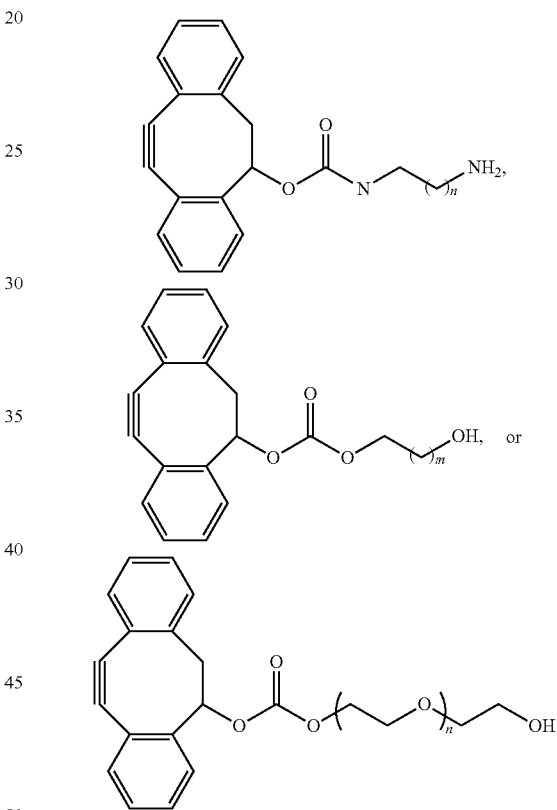

wherein n is an integer from 1 or more to 5 or less, and m is an integer from 1 or more to 11 or less.

* * * * *